(12) United States Patent
Mullin et al.

(10) Patent No.: US 10,758,130 B2
(45) Date of Patent: Sep. 1, 2020

(54) SINGLE SITE VITALS

(71) Applicant: Welch Allyn, Inc.

(72) Inventors: Matthew D. Mullin, Memphis, NY (US); David E. Quinn, Auburn, NY (US); John A. Lane, Weedsport, NY (US); Sean R. Karla, Syracuse, NY (US); Michael J. Anson, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 414 days.

(21) Appl. No.: 14/230,872

(22) Filed: Mar. 31, 2014

(65) Prior Publication Data
US 2015/0272452 A1 Oct. 1, 2015

(51) Int. Cl.
*A61B 5/00* (2006.01)
*A61B 5/0205* (2006.01)
*A61B 5/022* (2006.01)
*A61B 5/145* (2006.01)
*A61B 5/0225* (2006.01)
(Continued)

(52) U.S. Cl.
CPC ...... *A61B 5/02055* (2013.01); *A61B 5/02141* (2013.01); *A61B 5/02233* (2013.01); *A61B 5/02255* (2013.01); *A61B 5/02422* (2013.01); *A61B 5/14542* (2013.01); *A61B 5/6833* (2013.01); *A61B 5/01* (2013.01); *A61B 8/42* (2013.01); *A61B 8/4416* (2013.01); *A61B 8/488* (2013.01); *A61B 2562/225* (2013.01)

(58) Field of Classification Search
CPC .................................................. A61B 5/02141
See application file for complete search history.

(56) References Cited

U.S. PATENT DOCUMENTS 5,673,692 A 10/1997 Schulze et al.
6,454,718 B1 9/2002 Clift
(Continued)

FOREIGN PATENT DOCUMENTS

EP 0553372 8/1993
EP 0553372 A1 * 8/1993 ......... A61B 5/02055
(Continued)

OTHER PUBLICATIONS

Gao et al, A Simultaneous Monitoring System for Non-invasive Blood Pressure and Blood Oxygen Saturation, Blood Pressure and Blood Oxygen Saturation, Bioinformatics and Biomedical Engineering (iCBBE), 2010 4th International Conference, IEEE, 2010.*
(Continued)

*Primary Examiner* — Michael W Kahelin
*Assistant Examiner* — Sana Sahand
(74) *Attorney, Agent, or Firm* — Lee & Hayes, P.C.

(57) ABSTRACT

A system configured to determine a characteristic of a patient includes a plurality of sensors, wherein each sensor of the plurality of sensors is configured to noninvasively determine a respective parameter of the patient, and wherein the parameter determined by each sensor is different from parameters determined by remaining sensors of the plurality of sensors. Such a system also includes a connector having a passage configured to direct pressurized fluid therethrough, wherein the plurality of sensors is connected to the connector.

22 Claims, 8 Drawing Sheets

(51) Int. Cl.
*A61B 5/024* (2006.01)
*A61B 5/021* (2006.01)
*A61B 8/08* (2006.01)
*A61B 5/01* (2006.01)
*A61B 8/00* (2006.01)

(56) References Cited

U.S. PATENT DOCUMENTS

| | | | |
|---|---|---|---|
| 6,988,992 B2* | 1/2006 | Just | A61B 5/02233 600/485 |
| 8,182,443 B1 | 5/2012 | Kiani | |
| 9,241,642 B2* | 1/2016 | Quinn | A61B 5/02225 |
| 2004/0152961 A1 | 8/2004 | Carlson et al. | |
| 2005/0101843 A1* | 5/2005 | Quinn | G01K 13/002 600/300 |
| 2006/0074283 A1* | 4/2006 | Henderson | A61B 5/0059 600/315 |
| 2006/0291212 A1* | 12/2006 | Forsman | G10H 1/0016 362/276 |
| 2006/0293600 A1* | 12/2006 | Wawro | A61B 5/02141 600/490 |
| 2007/0129636 A1* | 6/2007 | Friedman | A61B 5/0205 600/481 |
| 2007/0185390 A1 | 8/2007 | Perkins et al. | |
| 2008/0027344 A1 | 1/2008 | Terry | |
| 2008/0051667 A1 | 2/2008 | Goldreich | |
| 2008/0221930 A1 | 9/2008 | Wekell et al. | |
| 2008/0243010 A1 | 10/2008 | Kulik | |
| 2008/0275317 A1 | 11/2008 | Cho et al. | |
| 2009/0018453 A1* | 1/2009 | Banet | A61B 5/02125 600/493 |
| 2009/0076343 A1 | 3/2009 | James et al. | |
| 2009/0099425 A1* | 4/2009 | Starr | A61B 5/02255 600/301 |
| 2009/0119124 A1 | 5/2009 | Kambaloor | |
| 2010/0049010 A1 | 2/2010 | Goldreich | |
| 2011/0046494 A1 | 2/2011 | Balji et al. | |
| 2011/0196211 A1 | 8/2011 | Al-Ali et al. | |
| 2011/0208013 A1 | 8/2011 | Phan et al. | |
| 2011/0224564 A1 | 9/2011 | Moon et al. | |
| 2011/0320216 A1 | 12/2011 | Kasmark | |
| 2012/0029323 A1* | 2/2012 | Zhao | A61B 5/0031 600/302 |
| 2012/0130203 A1 | 5/2012 | Stergiou et al. | |
| 2012/0271121 A1 | 10/2012 | Della Torre et al. | |
| 2013/0331716 A1 | 12/2013 | Wawro et al. | |

FOREIGN PATENT DOCUMENTS

| | | |
|---|---|---|
| EP | 1204367 B1 | 4/2007 |
| EP | 1867276 | 12/2007 |
| JP | H0739801 U * | 7/1995 |
| KR | 20090099147 | 9/2009 |
| KR | 100981137 B1 * | 9/2010 |
| WO | WO2008094489 | 8/2008 |
| WO | WO2010104952 | 9/2010 |
| WO | 2012/087634 A2 | 6/2012 |
| WO | WO2012161940 | 11/2012 |

OTHER PUBLICATIONS

Lin et al, Impact of blood pressure cuff inflation rates on flow-mediated dilatation and contralateral arm response, J. Human Hypertension, 26(1), pp. 35-40, 2012.*

Casavola et al, Blood flow and oxygen consumption with near-infrared spectroscopy and venous occlusion: spatial maps and the effect of time and pressure of inflation, J. Biomed. Opt., 5(3), pp. 269-276, 2000.*

Taenzer et al, A Comparison of Oxygen Saturation Data in Inpatients with Low Oxygen Saturation Using Automated Continuous Monitoring and Intermittent Manual Data Charting, Anesth Anlg, Feb. 2014, vol. 118, Issue 2, pp. 326-331.*

Cinar et al, Blood viscosity and blood pressure: role of temperature and hyperglycemia, American Journal of Hypertension, vol. 14, Issue 5, May 1, 2001, pp. 433-438.*

Galaxy technical specifications, Source: http://www.vicamedica.com/vicamedica/es/html_prods/down_productos/ESPgalaxying.pdf Date Accessed: Oct. 24, 2012.

Patient side module E-PSM, E-PSMP Source: http://www.gehealthcare.com/euen/patient_monitoring/docs/PatientSideModule_M1044263 eng.pdf Date Accessed: Oct. 24, 2012.

W.R. Dyck et al., "An integrated medical monitor for aeromedical use" Source: http://ftp.rta.nato.int/public/PubFullText/AGARD/CP/AGARD-CP-599/37SE5-31.pdf Presented at the AGARD AMP Symposium on Aeromedical Support Issues in Contingency Operations held in Rotterdam. The Netherlands, Sep. 29-Oct. 1, 1997, published in CP-599.

Shumei Gao, "A simultaneous monitoring system for non-invasive blood pressure and blood oxygen saturation", Bioinformatics and Biomedical Engineering (iCBBE), 2010 4th International Conference on Date of Conference: Jun. 18-20, 2010, Sch. of Mech. & Electr. Eng., Heilongjiang Univ., Harbin, China Yilin Song (pp. 4).

International Search Report and Written Opinion for PCT/US2015/021186, dated Jun. 25, 2015 (15 pages).

The Partial Supplementary European Search Report dated Oct. 26, 2017 for European Patent Application No. 15773169.6, 14 pages.

The Extended European Search Report dated Feb. 20, 2018 for European Patent Application No. 15773169.6, 12 pages.

The Extended European Search Report dated Mar. 25, 2019 for European Patent Application No. 18194362.2, 11 pages.

* cited by examiner

SINGLE SITE VITALS

TECHNICAL FIELD

This application is directed to systems and methods for monitoring a patient, and in particular, to systems and methods for determining patient characteristics based on a number of different parameters determined at a single measurement site.

BACKGROUND

Traditional non-invasive blood pressure monitoring devices operate by inflating a blood pressure cuff to a pressure above a patient's systolic blood pressure. For example, many physicians obtain blood pressure readings using blood pressure devices, such as sphygmomanometers, that include one or more tubes connecting the cuff to an inflation and/or measurement device. Because the systolic pressure is usually not known prior to inflation, the cuff must be inflated to such a pressure to ensure that the patient's arterial blood flow is completely occluded. Once above systole, pressure data may be collected and the cuff may be slowly deflated to enable the flow of blood through the artery to resume. Pressure data may also be collected during inflation and/or deflation of the cuff, and the collected data may be used to determine, for example, an average blood pressure of the patient.

Known temperature measurement devices may also utilize non-intrusive methods to determine a surface temperature of the patient's skin and/or to estimate a core temperature of the patient. For example, infrared thermometers or other like devices may be employed to measure radiation emitted by the patient's skin and/or by one or more blood vessels disposed just below the skin. Such thermometers may then calculate and/or otherwise determine the patient's core temperature based on the level of radiation collected.

Recently, advancements have been made to blood pressure measurement devices, temperature measurement devices, and other like patient monitoring devices utilized in healthcare facilities. Despite these advancements, however, determining the blood pressure, temperature, and other like parameters of the patient (such as blood oxygen saturation, heart rate, etc.) can be time-consuming and relatively intrusive. For example, two or more of the above parameters are typically measured separately during customary patient intake procedures, and generally, separate dedicated measurement devices are used to measure each parameter. The separate measurement of these parameters can unnecessarily extend the length of patient visits and, in some cases, may be uncomfortable for the patient. Additionally, since such measurements are performed separately, the parameter values determined through such measurements are not utilized to increase the accuracy or reliability of the separate value determinations.

The systems and methods described herein are directed toward overcoming the deficiencies described above.

SUMMARY

In an exemplary embodiment of the present disclosure, a system configured to determine a characteristic of a patient includes a plurality of sensors, wherein each sensor of the plurality of sensors is configured to noninvasively determine a respective parameter of the patient, and wherein the parameter determined by each sensor is different from parameters determined by remaining sensors of the plurality of sensors. Such a system also includes a connector having a passage configured to direct pressurized fluid therethrough, wherein the plurality of sensors is connected to the connector.

In another exemplary embodiment of the present disclosure, a system configured to determine a characteristic of a patient includes a plurality of sensors, wherein each sensor of the plurality of sensors is configured to noninvasively determine a respective parameter of the patient, and wherein the parameter determined by each sensor is different from parameters determined by remaining sensors of the plurality of sensors. Such a system also includes an inflatable cuff configured to selectively occlude a blood vessel of the patient, wherein the plurality of sensors is connected to the cuff.

In still another exemplary embodiment of the present disclosure, a system configured to determine a characteristic of a patient includes a patch configured to be worn by the patient, the patch having a first surface configured to contact the patient, and a second surface opposite the first surface. Such a system also includes a plurality of sensors connected to the patch, wherein each sensor of the plurality of sensors is configured to noninvasively determine a respective parameter of the patient, and wherein the parameter determined by each sensor is different from parameters determined by remaining sensors of the plurality of sensors. Such a system further includes a controller in communication with the plurality of sensors. The controller is configured to determine the characteristic of the patient based on at least a first parameter determined by a first sensor of the plurality of sensors and a second parameter determined by a second sensor of the plurality of sensors, wherein the characteristic is at least one of the first parameter as modified by the second parameter, or the second parameter as modified by the first parameter.

In a further exemplary embodiment of the present disclosure, a method of determining a characteristic of a patient includes noninvasively determining a plurality of parameters of the patient, wherein each parameter of the plurality of parameters is determined using a respective sensor of a plurality of sensors. The method also includes determining, via a controller in communication with the plurality of sensors, the characteristic of the patient based on at least a first parameter determined by a first sensor of the plurality of sensors and a second parameter determined by a second sensor of the plurality of sensors. In such a method, the characteristic is at least one of the first parameter as modified by the second parameter or the second parameter as modified by the first parameter.

DETAILED DESCRIPTION

Figure 1:
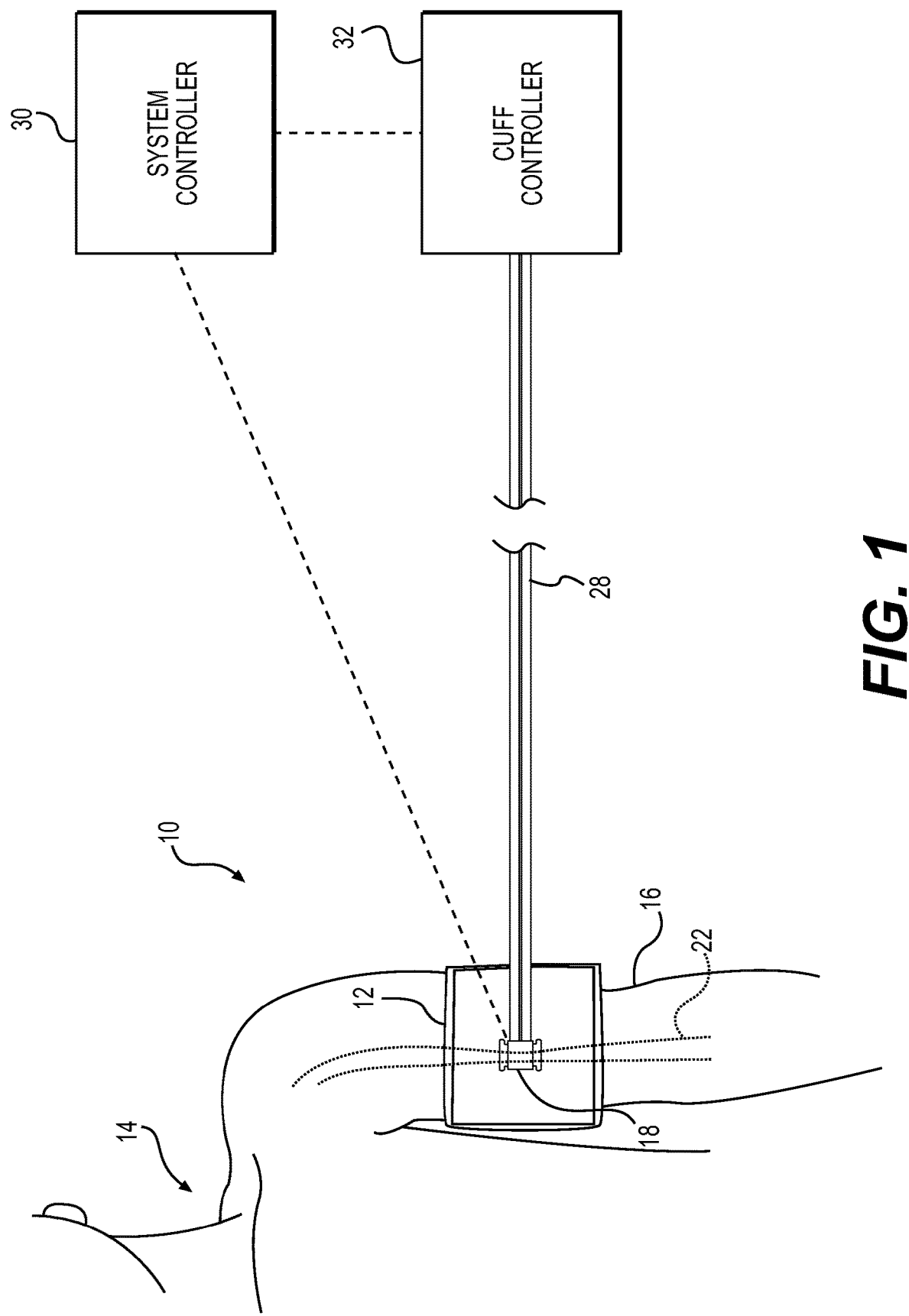
FIG. 1 illustrates a system according to an exemplary embodiment of the present disclosure.

FIG. 1 illustrates a system 10 configured to determine one or more characteristics of a patient according to an exemplary embodiment of the present disclosure. The system 10 can be configured to monitor a patient 14, and in some embodiments, to determine one or more parameters of the patient 14. Such parameters may include, for example, a systolic blood pressure, a diastolic blood pressure, a mean arterial blood pressure, a venous blood pressure, a heart rate, a blood oxygen saturation ("SpO$_2$"), a temperature, and/or any other like metric of patient health. As will be described in greater detail below, the system 10 may be configured to determine one or more characteristics of the patient 14 based on individual parameters or on a combination of such parameters. For example, the system 10 may be configured to determine a first parameter and a second parameter, and the system 10 may be configured to determine a characteristic of the patient 14 based on the first and second parameters. In such embodiments, the determined characteristic may comprise any of the parameters described above as modified by one or more additional parameters. For instance, if in the above example, the first parameter comprises a blood pressure, and the second parameter comprises a temperature, the system 10 may be configured to determine a blood pressure (i.e., a characteristic) of the patient 14 based on the determined blood pressure (i.e., the first parameter) as modified by the determined temperature (i.e., the second parameter) and/or by one or more additional parameters. Additionally, the system 10 may be configured to determine a temperature (i.e., a characteristic) of the patient 14 based on the determined temperature (i.e., the second parameter) as modified by the determined blood pressure (i.e., the first parameter) and/or by one or more additional parameters.

As shown in at least FIG. 1, the system 10 can include any type of wrap, blood pressure cuff, and/or other like inflatable device (hereinafter "cuff 12") configured to at least to partially occlude the movement of blood through a vein, artery, and/or other blood vessel 22 of the patient 14. In some embodiments, the cuff 12 can be configured to completely occlude the blood vessel 22, and the blood vessel 22 may be, for example, the brachial artery. For example, the cuff 12 may be inflated to any known occlusion pressure, and at such an occlusion pressure, the blood vessel 22 may be at least partially occluded. The cuff 12 may also be deflated to a deflated pressure below (i.e., less than) the occlusion pressure, and at such a pressure, the blood vessel 22 may be substantially unoccluded. Although shown in FIG. 1 as surrounding the upper arm of patient 14, the cuff 12 may be adapted for placement on or about any suitable limb 16 and/or other portion of the patient's body, including, for example, a wrist, a finger, an upper thigh, or an ankle. In addition, one or more cuffs 12 could be disposed at different locations about and/or on the patient 14 for use with the system 10.

The exemplary cuffs 12 of the present disclosure may be formed from any medically approved material known in the art. Such materials may be highly flexible, durable, and suitable for contact with, for example, the skin of the patient 14. For example, as shown in at least FIG. 2, the cuff 12 may include at least two surfaces exposed on an exterior of the cuff 12, such as, for example, an outer surface 34 and an inner surface 36, and at least one of the outer and inner surfaces 34, 36 may be configured for contact with the limb 16 of the patient 14 during inflation and deflation of the cuff 12. In some of the embodiments described herein, the inner surface 36 is configured for contact with the limb of the patient 14. Further, the cuff may include at least two surfaces associated with an interior of a cuff, such as, for example two surfaces from different structures of the cuff comprising a portion of a bladder (as described in more detail below) of the cuff 12.

The materials utilized to construct the cuff 12 may also be at least one of tear-resistant, fluid-impermeable, and recyclable. Such materials may include, for example, paper, cloth, mesh and/or polymers such as polypropylene or polyethylene. In still further exemplary embodiments, such materials may be coated and/or otherwise treated with one or more additives that cause the material to become biodegradable within a desired time interval (e.g., within 2 to 3 months). Each of the exemplary cuffs 12 described herein may have a respective length, width, and inflated height suitable for use with a particular patient 14. For example, a first cuff 12 intended to be used with an adolescent patient 14 may have a first deflated length and a first deflated width, and a second cuff 12 intended for use with an adult patient 14 may have a corresponding second deflated length and second deflated width. In such an exemplary embodiment, the first deflated length may be less than the second deflated length and the first deflated width may be less than the second deflated width. In exemplary embodiments, inflated lengths and widths of the exemplary cuffs 12 described herein may be different than the corresponding deflated lengths and widths.

The cuff 12 may include one or more bladders (not shown) or other like inflatable devices. Such a bladder may be formed from a single piece of material or, alternatively, from two or more pieces of material that are joined together through heat sealing, ultrasonic or radio frequency (RF) welding, adhering, and/or other like processes. In still further exemplary embodiments, the cuff 12 may form one or more inflatable pockets that perform the same functions as a bladder. In such exemplary embodiments, the bladder may be omitted. It is understood that the cuff 12 and/or bladder may be inflatable to an occlusion pressure of approximately 160 mm Hg or greater to assist in at least partially occluding the blood vessel 22.

Figure 2:
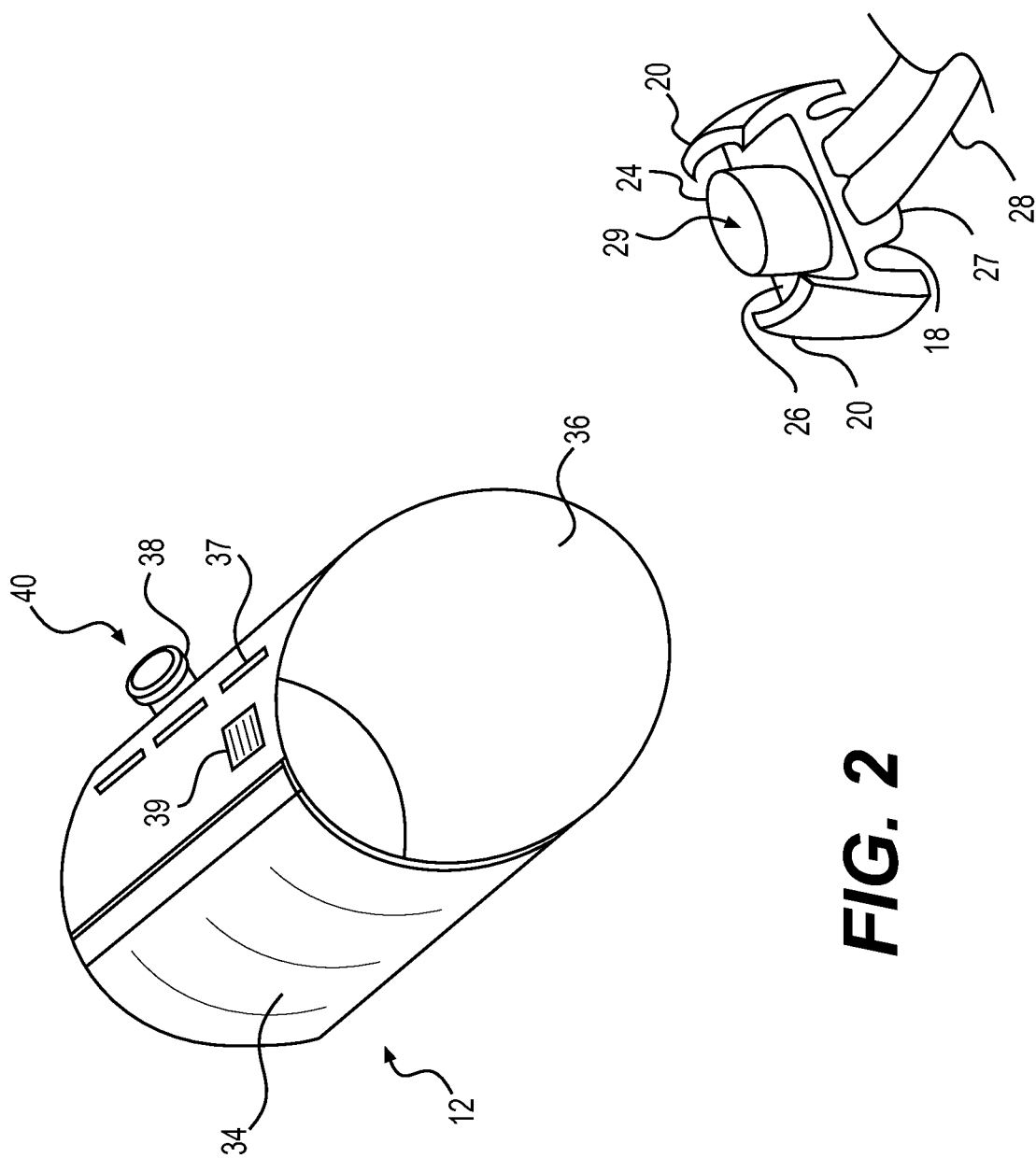
FIG. 2 illustrates an exemplary connector and an exemplary cuff associated with the system of FIG. 1.

As illustrated in FIG. 2, the cuff 12 may also include one or more ports 38 fluidly connected to the internal pocket or bladder to assist with inflation and/or deflation thereof. In exemplary embodiments, the port 38 may comprise an open-ended substantially cylindrical structure, and a portion of the port 38 may protrude from the outer surface 34 of the cuff 12. Such an exemplary port 38 may include, for example, a circumferential shelf, flange, ridge, shoulder, and/or other like structure to facilitate mechanical and/or fluid connection with one or more known fittings, adapters, and/or other like cuff connectors 18. For example, the port 38 may be shaped, sized, and/or otherwise configured to mate with a corresponding cuff connector 18, and the cuff connector 18 may be fluidly connected to a bulb, pump, and/or other like cuff controller 32 utilized to inflate and/or deflate the cuff 12. Additional details concerning exemplary port designs are provided in co-owned U.S. Pat. No. 6,422,086, entitled "Low Profile Pressure Measuring Device," and co-owned U.S. Pat. No. 8,535,233, entitled "Blood Pressure Monitoring Apparatus," the entire disclosures of which are incorporated herein by reference.

As will be described in greater detail below with respect to FIGS. 2 and 3, the cuff connector 18 may comprise any fitting or other like device configured to releasably and/or otherwise removably connect to the port 38 and to direct pressurized fluid to and/or from the cuff 12 via the port 38. The cuff connector 18 may be configured to releasably fluidly connect to the cuff 12 via the port 38, and may include one or more moveable, biased, spring-loaded, and/or otherwise adjustable components configured to facilitate a removable connection with the port 38. For example, the cuff connector 18 may include one or more arms, latches, hooks, prongs, snap connectors, and/or other like retention components 20 (FIG. 2) configured to engage the port 38, and to apply a retention force to the port 38. In such an embodiment, the retention component 20 may engage the port 38 and may mechanically releasably connect the cuff connector 18 to the cuff 12. The cuff connector 18 may further include one or more O-rings, gaskets, seals, or other like components (not shown) to assist in forming a substantially fluid-tight connection with the port 38. In exemplary embodiments, the port 38 may also include one or more O-rings, gaskets, seals, or other like components to assist in forming such a substantially fluid-tight connection with the cuff connector 18.

To further assist in forming a fluid connection with the cuff 12, the cuff connector 18 may include one or more portions extending therefrom and configured to mate with the port 38 of the cuff 12. For example, such a portion may comprise a substantially hollow protrusion or other like extension 24. The extension 24 may include one or more passages 29 configured to direct fluid from and/or to the cuff 12. For example, the port 38 may include one or more corresponding passages 40, and fluid may pass between the passages 29, 40 when the cuff connector 18 is fluidly connected to the port 38. In exemplary embodiments, the extension 24 may extend substantially perpendicularly from, for example, a top surface 26, a side surface, or a bottom surface 27 of the cuff connector 18. The extension 24 may be shaped, sized, positioned, and/or otherwise configured to accept a portion of the port 38 therein when the cuff connector 18 is mechanically and/or fluidly connected to the cuff 12. Alternatively, the extension 24 may be shaped, sized, positioned, and/or otherwise configured to substantially surround the port 38, and may overlay the port 38 when the cuff connector 18 is connected to the cuff 12. In still further embodiments, the extension 24 may be shaped sized, positioned, and/or otherwise configured for insertion into the port 38, such as for insertion at least partially into the passage 40, when the cuff connector 18 is connected to the cuff 12.

With continued reference to FIG. 1, the pressure or volume of fluid within the cuff 12 may be controlled by the cuff controller 32 fluidly connected and/or otherwise operably associated with the cuff 12 via the cuff connector 18. For example, the system 10 may include an automatic cuff controller, a manual cuff controller, and/or any other like cuff controller 32 known in the art. In such embodiments, the system 10 may further include one or more flexible hoses 28 fluidly connecting the cuff controller 32 and the cuff connector 18. Additional details concerning cuff controllers are provided in co-owned U.S. Pat. No. 8,123,694, entitled "Electro Pneumatic Interface for Blood Pressure System," the entire disclosure of which is incorporated herein by reference.

The various cuff controllers 32 of the present disclosure can include a pump or similar device configured to inflate and/or deflate the cuff 12. For example, an automatic cuff controller 32 could be controlled by a protocol or program stored in a memory associated with the cuff connector 18 to supply the cuff 12 with a fluid, such as air, to increase the pressure or volume within the cuff 12. Such an automatic cuff controller 32 may also be operatively connected and/or otherwise in communication with a system controller 30. In such embodiments, the automatic cuff controller 32 may be configured to selectively inflate and deflate the cuff 12 in response to one or more control signals received from the system controller 30.

In additional exemplary embodiments, a manual cuff controller 32 may be configured to selectively inflate and deflate the cuff 12, and to thereby substantially occlude and unocclude the blood vessel 22, in ways similar to the automatic cuff controller described above. However, a manual cuff controller 32 may be hand and/or otherwise manually operated by a user of the system 10 to inflate and deflate the cuff 12. A manual cuff controller 32 may comprise any manually operated device configured to supply fluid to and release fluid from the cuff 12. In exemplary embodiments, a manual cuff controller 32 may comprise a manually operated bulb, pump, or other like device commonly associated with conventional manual sphygmomanometers. In such embodiments, the manual cuff controller 32 may also include one or more valves (not shown) or other like flow control devices configured to maintain fluid, such as air, within the cuff 12 during inflation thereof, and to facilitate the gradual release of such fluid from cuff 12 during deflation. The valve may be manually controlled by the user to regulate the flow of air into and out of the cuff 12 during, for example, auscultation. In exemplary embodiments, the valve may comprise a manually controlled check valve or other like device. It is understood that the system 10 may comprise any known oscillometric or auscultation system, and that the system 10 may be configured to perform and/or otherwise employ any known oscillometric or auscultation methods.

Figure 3:
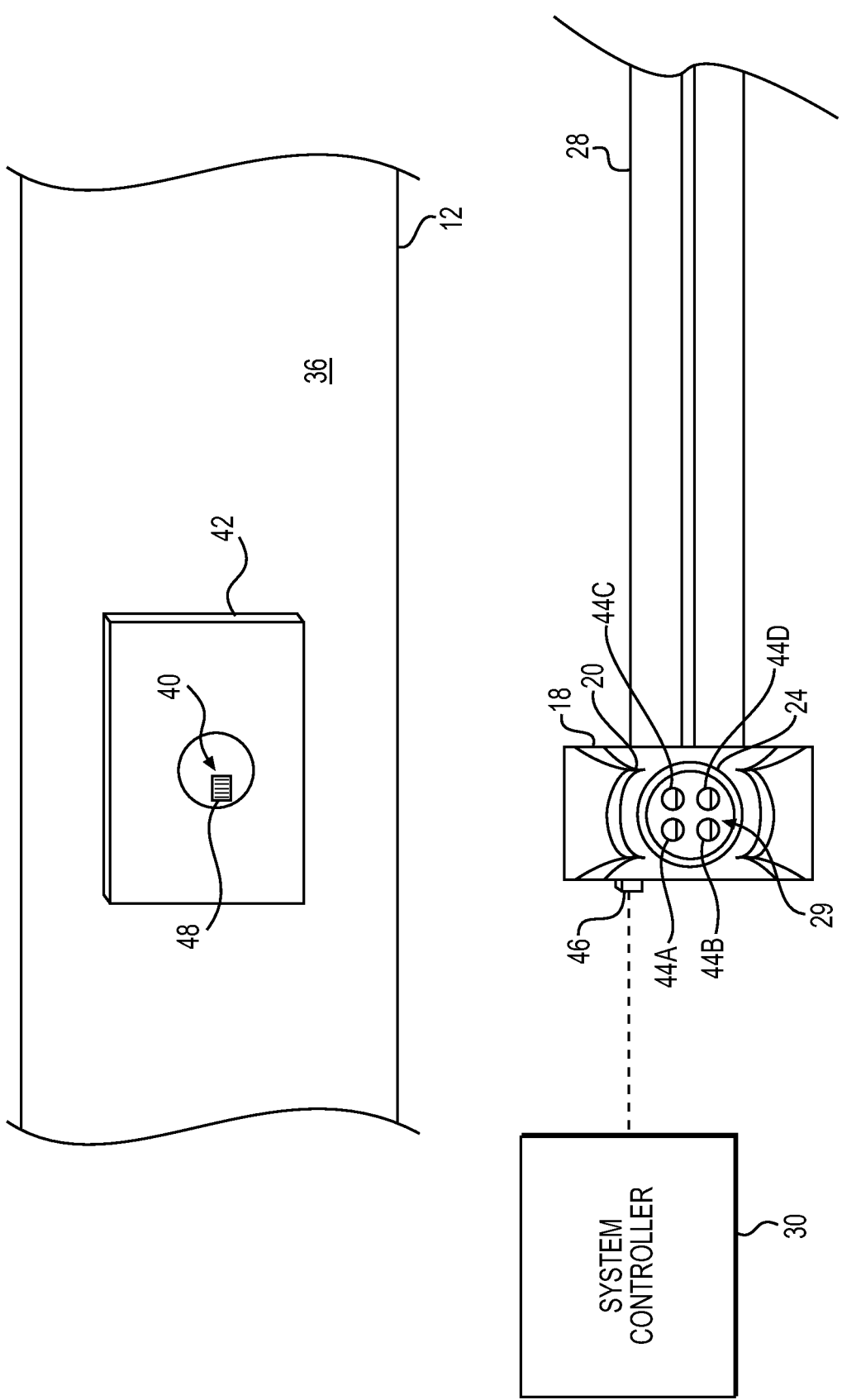
FIG. 3 illustrates a portion of the connector and cuff shown in FIG. 2.

As shown in at least FIG. 3, the system 10 may also include one or more sensors configured to noninvasively determine respective parameters of the patient 14. For example, the system 10 may include a plurality of sensors 44a, 44b, 44c, 44d . . . 44n (collectively referred to herein as "sensors 44"). In some embodiments, each sensor of the plurality of sensors 44 may be configured to noninvasively determine at least one respective parameter of the patient 14, and in such embodiments, the parameter determined by each sensor may be different from parameters determined by remaining sensors of the plurality of sensors 44. For instance, a first sensor 44a may be configured to determine a blood pressure of the patient 14, a second sensor 44b may be configured to determine a temperature of the patient 14, a third sensor 44c may be configured to determine an $SpO_2$ of the patient 14, and a fourth sensor 44d may be configured to determine a heart rate of the patient 14. It is understood that the system 10 may include greater than or less than the four sensors 44 illustrated in FIG. 3, and additional sensors 44 may include, for example, radio-frequency identification (RFID) readers, barcode scanners, pixel arrays, cameras, Doppler sensors, proximity sensors, microwave temperature antennae, accelerometers, gyroscopes, and/or any other known sensor. For example, in an embodiment in which one or more such sensors 44 includes a camera or other like imaging device, such a camera may be configured to capture and/or generate one or more images of the patient 14, the limb 16, and/or other like measurement sites. The camera may also capture and/or generate one or more images of at least a portion and/or surface of the cuff 12 providing, for example, an indication of a parameter associated with the cuff 12 and/or the patient 14. In such embodiments, the cuff 12 may include, for example, a component that is temperature sensitive. Such a component of the cuff 12 may, for example, turn different colors when exposed to different temperatures. For example, such a component may take on a first color when the component is disposed proximate to and/or in contact with a measurement site having a first temperature. The component may also take on a second color different from the first color when the component is disposed proximate to and/or in contact with the same or a different measurement site having a second temperature different from the first temperature. In such embodiments, the camera may determine each color and/or the change in color. The camera may also send information to the system controller 30 indicative of such colors and/or such change in colors, and the system controller 30 may be programed to determine a temperature and/or a range of temperatures of the measurement site based on such information. Further, such sensors 44 may be operable in the visible, thermal, infrared, and/or any other radiation band. Such sensors 44 may also comprise one or more sound sensors or other like auditory devices.

In an exemplary embodiment, at least one of the sensors 44 may comprise a temperature sensor, such as a thermopile, thermocouple, and/or thermistor, configured to sense a temperature associated with the patient 14. For example, at least one of the sensors 44 may be configured to sense, detect, measure, estimate, calculate, and/or otherwise determine a temperature of a measurement site of the patient 14 with which the sensor has been placed in contact and/or with which the sensor has been placed proximate to. For example, each of the sensors 44 may have a respective field of view, and the sensors 44 may be configured to determine respective parameters of the patient 14 when the measurement site of the patient 14 has been placed within the field of view of the respective sensor. It is understood that exemplary measurement sites may include skin or body surfaces at various locations on the arm, leg, finger, or other limbs 16 of the patient 14. In further exemplary embodiments, such measurement sites may also include a forehead, ear, oral cavity, rectal cavity, axilla area, inner canthal region, sinus region, eye region, and/or any other known or easily accessible outer surface of the patient 14. For example, in the embodiment shown in FIGS. 1-3, such measurement sites may be within the field of view of the sensors 44 when the cuff 12 is disposed around the limb 16 of the patient 14 and the cuff connector 18 is connected to the port 38. In such embodiments, the sensors 44 may be configured to determine parameters of the patient 14 at the measurement site via an interrogation component of the cuff 12. Such an interrogation component will be described in greater detail below.

In exemplary embodiments, at least one of the sensors 44 may comprise an infrared temperature sensor such as, for example, a thermopile and/or other like infrared-based temperature sensing components. Such a sensor may be configured to convert thermal energy into electrical energy, and may comprise two or more thermocouples connected in series or in parallel. Such components may be configured to generate an output voltage proportional to a local temperature difference and/or temperature gradient. In an exemplary embodiment in which at least one of the sensors 44 comprises at least one thermopile, the system 10 may comprise an infrared thermometer. In such embodiments, at least one of the sensors 44 may be configured to receive and/or emit radiation, such as thermal and/or infrared radiation. For example, at least one of the sensors 44 may be configured to sense, detect, collect, and/or otherwise receive radiation emitted by the patient 14. Such radiation may be emitted by, for example, the blood vessel 22 and/or any of the patient measurement sites described herein. In such embodiments, the sensor may be configured to collect the radiation, and to send a signal to the system controller 30 indicative of the collected radiation. The system controller 30 may utilize the received signal for any number of known functions. For example, the system controller 30 may be configured to estimate, infer, calculate, and/or otherwise determine a core temperature and/or other like characteristic of the patient 14 based on the signal and/or one or more additional inputs.

In further embodiments, at least one of the sensors 44 may comprise an array of pixels and/or other like sensing elements configured to determine a temperature of the patient 14. In exemplary embodiments, an array of sensing elements may include one or more infrared sensing elements configured to sense a temperature of the measurement site of the patient 14. Such an array of sensing elements, and any of the infrared temperature sensors described herein, may be configured to determine a temperature of the measurement site without contacting the patient 14 with the sensor. In exemplary embodiments, one or more of the sensing elements described herein may be configured to determine more than one temperature of the measurement site. For example, an array of sensing elements included in at least one of the sensors 44 may be configured to determine a temperature at a respective area of the measurement site. In such embodiments, the system controller 30 and/or the sensor may be configured to generate a two or three-dimensional temperature measurement of the patient 14 and, in particular, of the outer surface of the patient 14 at the measurement site.

In additional embodiments, at least one of the sensors 44 may be configured to determine one or more of an oscillation signal strength, a cumulative cycle count of the cuff 12, a volume of the cuff 12, an occlusion pressure of the cuff 12, a cumulative time associated with the cuff 12 being inflated to a reference volume and/or pressure. In such embodiments, at least one of the sensors 44 may comprise devices including, but not limited to, one or more of a pressure sensor, a hygrometer, a pneumatic sensor, and/or a timer. In some embodiments, at least one of the sensors 44 can be configured to receive a signal associated with an at least partially occluded blood vessel 22 of patient 14. Such an input signal can arise from blood movement through the partially occluded blood vessel 22 or from a signal associated with an occluded blood vessel. In such embodiments, the sensor could sample various aspects or characteristics of the blood vessel 22 multiple times at various intervals. In additional exemplary embodiments, the sensor could provide an indication of blood vessel movement, such as, for example, oscillations arising from vascular expansion or contraction. Such oscillations may produce a signal that is detected by the sensor, and the strength of such an oscillation signal may be used to determine a hemodynamic parameter of the patient 14, such as blood pressure. For example, at least one of the sensors 44 could be configured to detect an occlusion pressure or volume of cuff 12 that may vary periodically with the cyclic expansion and contraction of the blood vessel 22 of patient 14.

In further exemplary embodiments, at least one of the sensors 44 may comprise an $SpO_2$ sensor, a heart rate monitor, a Doppler sensor, and/or any other like sensor known in the art. For example, at least one of the sensors 44 may be configured to determine an oxygen concentration of blood passing through the blood vessel 22. Such determinations may be made substantially continuously, and/or at any interval known in the art. In such exemplary embodiments, at least one of the sensors 44 may comprise any known photoplethysmography components and/or other like pulse oximetry devices configured to noninvasively determine blood oxygen concentration and/or other like parameters associated with blood passing through the blood vessel 22. For example, at least one of the sensors 44 may include a pulse oximeter configured to illuminate at least a portion of the skin at the measurement site, and to sense, measure, detect, and/or otherwise determine a change in light absorption at the measurement site. In such an embodiment, the pulse oximeter may monitor and/or otherwise determine the profusion of blood to the dermis and subcutaneous tissue of the skin at the measurement site. Further, in such exemplary embodiments, at least one of the sensors 44 may comprise a light-emitting diode (LED) or other like light source configured to illuminate the skin at the measurement site. Further, at least one of the sensors 44 may include a photodiode or other like components configured to determine the amount of light emitted by the light source that is either transmitted or reflected thereto.

It is understood that in some embodiments, one or more of the pulse oximetry devices described above may also be configured to determine the heart rate, respiration, and/or cardiac cycle of the patient 14. Alternatively, in further exemplary embodiments at least one of the sensors 44 may comprise a dedicated heart rate monitor, cardiac cycle monitor, respiration monitor, and/or other like device.

In additional exemplary embodiments, at least one of the sensors 44 may be configured to read, scan, sense, detect, and/or otherwise input information associated with the cuff 12. Such information may include, for example, an occlusion efficiency that is particular to the actual cuff 12 being used, or an occlusion efficiency associated with the type, size, design, model, and/or style of cuff 12 being used. It is understood that the type, size, design, model, and/or style of the cuff 12 may be parameters that are unique or particular to the actual cuff 12 being used. For example, such parameters may include and/or may be indicative of the length, width, inflated height, and/or other dimensions of the cuff 12, the shape of the cuff 12, the number of bladders included in the cuff 12, the length, width, and/or inflated height of such bladders, the maximum inflated volume of the cuff 12, materials used to construct the cuff 12, and whether the cuff 12 is intended for use with a child, adolescent, adult, elderly, and/or bariatric patient 14, among other things. In such exemplary embodiments, at least one of the sensors 44 may comprise an RFID reader, a barcode reader, a magnetic ink character recognition (MICR) reader, a conductance sensor, a resistance sensor, a magnetic sensor, and/or any other like reading device known in the art.

Such a sensor may also be configured to sense, scan, detect, and/or otherwise read information carried by one or more information features 39 associated with the cuff 12. In addition to standard text, such information features 39 may comprise one of an RFID tag, a barcode, MICR printing, a conductive, resistive, and/or magnetic strip of material, and/or other known means for providing information. For example, such information features 39 may communicate an occlusion efficiency of the cuff 12 to at least one of the sensors 44 and/or to a user of the system 10. Such information features 39 may also communicate an identification parameter particular to the cuff 12. Such an identification parameter may be indicative of, for example, the type, size, design, model, and/or style of the cuff 12 being used. Such an identification parameter may also comprise, for example, a serial number, a model number, a part number, and/or any other like information enabling the particular cuff 12 to be identified for purposes of tracking or recording, for example, a cumulative cycle count, an age of the cuff, and/or any of the other parameters described herein.

Moreover, such an identification parameter may be unique to the patient 14. For example, the identification parameter may comprise a patient identifier including the name, address, social security number, patient identification number, age, weight, height, gender, ethnicity, status, existing condition, and/or other characteristics or information particular to and/or otherwise identifying the patient 14.

One or more such information features 39 may be disposed on the outer surface 34 of the cuff 12 for reading by the sensor or, alternatively, may be embedded within and/or formed integrally with the cuff 12. Alternatively and/or in addition, an information feature 48 including at least one of the patient identifiers described above may be disposed at least partially within the field of view of at least one of the sensors 44 when the connector 18 is connected to the port 38. As will be described in greater detail below, such an information feature 48 may be disposed on the inner surface 36 and/or on a component of the inner surface 36. In any of the embodiments described herein, at least one of the sensors 44 and/or components of the system 10 in communication with the sensors 44 may employ various pattern recognition software, identification software, and/or other like control hardware/software to assist in reading the information provided by the information features 39, 48. In such embodiments, the information feature 39, 48 may include text, characters, numerals, figures, and/or other indicia that is screen printed, encoded, and/or otherwise viewable on a surface thereof. Alternatively, such indicia may be printed, encoded, and/or otherwise disposed on the inner surface 36 and/or the outer surface 34 of the cuff 12.

As shown in FIG. 3, one or more of the sensors 44 associated with the system 10 may be connected to the cuff connector 18. For example, at least one of the sensors 44 may be disposed proximate, adjacent, and/or at least partially within the extension 24 and/or the passage 29. In such exemplary embodiments, at least one of the sensors 44 may be configured to determine one or more respective parameters of the patient 14 via the extension 24 and/or the passage 29 when, for example, the cuff connector 18 is connected to the port 38. For example, when the cuff connector 18 is connected to the port 38, at least a portion of the measurement site may be disposed within the field of view of at least one of the sensors 44. Further, when the cuff connector 18 is connected to the port 38, at least one of the sensors 44 may be disposed opposite the port 38. Accordingly, at least one of the sensors 44 may be configured to determine one or more respective parameters of the patient 14 when the cuff connector 18 is removably connected to the cuff 12 via the port 38.

In exemplary embodiments, the cuff 12 may include one or more alignment markers 37 configured to align at least one of the sensors 44 with the blood vessel 22 of the patient 14 when the cuff 12 is disposed around the limb 16 of the patient 14. For example, when disposing the cuff 12 around the limb 16, a healthcare professional may visually align one or more such alignment markers 37 with the blood vessel 22 such that the port 38 substantially overlays the blood vessel 22. In such embodiments, at least one of the alignment markers 37 may extend linearly along the outer surface 34 of the cuff 12 and may be substantially aligned with the port 38 along a longitudinal axis (not shown) of the cuff 12. By aligning the one or more alignment markers 37 with the blood vessel 22 in this way, the healthcare professional may ensure that the sensors 44 connected to the cuff connector 18 may substantially overlay and/or they otherwise be in alignment with the blood vessel 22 when the cuff connector 18 is connected to the port 38. In an exemplary embodiment, aligning the one or more alignment markers 37 with the blood vessel 22 may also ensure that the blood vessel 22 is disposed at least partially within the field of view of at least one of the sensors 44 when the cuff connector 18 is connected to the port 38. In exemplary embodiments, the alignment markers 37 may comprise one or more visual, tactile, and/or other indicia, and such alignment markers 37 may be printed on, adhered to, and/or formed integrally with at least the outer surface 34 of the cuff 12.

The cuff 12 may also include one or more interrogation components 42 configured to assist the sensors 44 in determining respective parameters of the patient 14. In exemplary embodiments, such interrogation components 42 may comprise one or more windows, lenses, and/or other like optical devices positioned on, formed integral with, and/or disposed substantially within the cuff 12. For example, such an interrogation component 42 may be disposed substantially flush and/or coplanar with the inner surface 36 of the cuff 12 as shown in FIG. 3. Such interrogation components 42 may be disposed, for example, at least partially along a portion of the inner surface 36, and may be configured to assist in, for example, focusing, directing, and/or otherwise transmitting radiation to the sensors 44 for collection. In additional exemplary embodiments, such interrogation components 42 may assist in focusing, directing, and/or otherwise transmitting radiation emitted by the sensors 44. Such interrogation components 42 may also assist in protecting the thermopile, thermocouple, thermistor, and/or other sensor components during use of the system 10, and may assist in forming a substantially fluid tight compartment (not shown) within the cuff 12 and/or between the cuff 12 and the sensors 44 to protect sensor components from contact with bodily fluids, cleaning solutions, and/or other liquids. It is understood that such interrogation components 42 may be substantially transparent to assist in the transmission of infrared and/or other types of radiation. In exemplary embodiments, the interrogation components 42 may comprise one or more convergent, collimating, and/or divergent lenses. In any of the embodiments described herein, the interrogation components 42 may be made of flexible materials such that the interrogation components 42 may conform to the shape of the limb 16 of the patient 14 as the cuff 12 is disposed around, inflated, and/or deflated on the limb 16.

In exemplary embodiments of the system 10 in which the sensors 44 are connected to the cuff connector 18, one or more of the interrogation components 42 may be disposed at least partially within a field of view of at least one of the sensors 44 when the cuff connector 18 is connected to the port 38. In such embodiments, the one or more interrogation components 42 may be substantially transparent to any radiation emitted from and/or received by the sensors 44 so as not to interfere with the transmission of radiation from or to the sensors 44. Additionally, as described above, one or more of the interrogation components 42 may be configured to assist with the transmission of such radiation. As shown in at least FIG. 3, at least a portion of the one or more interrogation components 42 may be disposed on the inner surface 36, and may overlay at least a portion of the port 38 and/or the passage 40. In still further embodiments, the cuff 12 may include more than one interrogation component 42. For example, the cuff 12 may include a first interrogation component on and/or embedded substantially within the outer surface 34 and a second interrogation component on and/or embedded substantially within the inner surface 36 that is substantially aligned with the first interrogation component. In such embodiments, the first interrogation component may substantially overlay the second interrogation component such that the measurement site may be viewed by a user of the system 10 through the first and second interrogation components when the cuff 12 is disposed, for example, around the limb 16 of the patient 14. In such embodiments, one or more sensors 44 and/or other medical devices may be used to determine various parameters of the patient 14 through the first and second interrogation components. For example, the sensors 44 may be utilized to sense the measurement site via the overlayed interrogation components with such sensors 44 that could be associated or disassociated with, for example, the cuff connector 18, the hose 28, and/or the cuff 12.

Further, as noted above, in exemplary embodiments the cuff 12 may include one or more information features comprising, for example, a patient identifier providing information particular to the patient 14 with which the cuff 12 is associated. For example, the cuff 12 may remain disposed on the limb 16 of the patient 14 as the patient 14 passes to various locations within a healthcare facility. In such situations, the patient identifier of the information features may assist in identifying the patient 14 at each new location within the healthcare facility. In addition to and/or as an alternative to the one or more information features 39 associated with the outer surface 34 of the cuff 12, in further embodiments, one or more information features 48 may be disposed at least partially within the field of view of at least one of the sensors 44 when the cuff connector 18 is connected to the port 38. For example, in exemplary embodiments of the system 10 in which the sensors 44 are connected to the cuff connector 18, one or more information features 48 may be disposed on the inner surface 36 and/or on the interrogation component 42. In such embodiments, at least one of the sensors 44 may be configured to scan, read, observe, and/or otherwise determine information provided by the patient identifier of the information feature 48 when the cuff connector 18 is connected to the port 38. As described above, such information may be unique and/or otherwise particular to the patient 14. In still further embodiments, it is understood that such an information feature 48 may be disposed and/or otherwise integrally formed with the inner surface 36.

In further embodiments, the system 10 may include one or more transmitters, network devices, routers, Bluetooth® devices, WiFi® devices, radio devices, and/or other like communication device 46 configured to transmit data to a remote location and/or to a remote device. In such embodiments, the communication device 46 may enable the transmission of information to or from the system controller 30. It is understood that such communication devices 46 may facilitate the transmission of such information via wired or wireless means. For example, in any of the embodiments described herein, one or more components of the system 10, such as the system controller 30, may be disposed remote from a remainder of the components of the system 10. In such embodiments, for example, the system controller 30 may be disposed in a different location of a healthcare facility than the cuff 12, the sensors 44, or other components of the system 10. Alternatively, in further embodiments, the system controller 30 may be in a first healthcare facility and a remainder of the components of the system 10 may be located in a second healthcare facility different from the first facility. In such embodiments, the various components of the system 10 may be in communication and/or otherwise operably connected via the communication devices 46 described herein. As shown in FIG. 3, such a communication device 46 may be connected to the cuff connector 18 at any convenient location. Additionally, the communication device 46 may be operably and/or otherwise connected to at least one of the sensors 44. Such a communication device 46 may be configured to provide signals from each respective sensor 44a, 44b, 44c, 44d . . . 44n to the system controller 30 indicative of the parameter determined by the respective sensor. Likewise, the system controller 30 may include a corresponding communication device configured to receive such signals and/or transmit control signals to the sensors 44.

In exemplary embodiments, the system controller 30 may comprise and/or otherwise include one or more processors, microprocessors, programmable logic controllers, and/or other like components configured to control one or more operations of the cuff 12, the cuff controller 32, and/or the sensors 44. For example, the controller 30 can control inflation and/or deflation of the cuff 12 via control of the cuff controller 32. The system controller 30 may also calculate, estimate, and/or otherwise determine one or more characteristics of the patient 14 based on one or more of the parameters determined by the sensors 44. This determination may be based on, for example, one or more output signals received by the system controller 30 from the sensors 44. In example embodiments, information contained in such output signals may be used by the system controller 30 as inputs into one or more algorithms, neural networks, or other like controller components and the determined characteristic may comprise an output of such components.

In any of the embodiments described herein, the sensors 44 may be in communication with and/or otherwise operably connected to the controller 30 in any known way. For example, the sensors 44 may be wirelessly connected to the system controller 30 via one or more communication devices associated with the sensors 44 and/or the system controller 30. Such exemplary communication devices will be described in greater detail below. Additionally or alternatively, the sensors 44 may be connected to the system controller 30 via one or more wires, leads, or other like physical and/or electrical connections. For example, one or more respective wires (not shown) may extend from the sensors 44 to the system controller 30 to facilitate such a connection. Such wires may be routed from the sensors 44 to the system controller 30 in any convenient way, and in example embodiments, such such wires may extend substantially within and/or along at least one of the flexible hoses 28. In still further embodiments, the sensors 44 may communicate bidirectionally with the system controller 30 via any known acoustic or optical means. In such embodiments, example acoustic communication between the sensors 44 and the system controller 30 may be at least partially transmitted via at least one of the flexible hoses 28.

Additionally, the sensors 44 of the present disclosure may be powered by any known power supply or other like means. For example, in embodiments in which the sensors 44 are physically and/or electrically connected to the system controller 30, the system controller 30 may provide power to the sensors 44, such as from a battery or other like power supply of the system 10, via such a connection. In further embodiments, the sensors 44 may be powered by one or more batteries directly connected to the sensors 44. In still further embodiments, the sensors 44 may be powered by one or more solar cells connected to the sensors 44. In additional embodiments, the sensors 44 may be powered via one or more components configured to convert thermal energy from the patient 14 into useable power.

Further, the system controller 30 may include any known memory (not shown) associated therewith, and one or more of the algorithms, neural networks, or other like controller components described herein may be stored in the memory of the system controller 30. The memory may include, for example, a hard drive, a thumb drive, and/or any other like fixed or removable storage device known in the art. Such memory may comprise random access memory, read-only memory, transient memory, non-transient memory, and/or any other like information storage means. In such embodiments, the memory may be configured to store signals, data, values, curves, thresholds, and/or any other like information received from the sensors 44. The memory may also be configured to store signals, data, values, thresholds, curves, and/or any other like information determined by the system controller 30 during the various operations described herein. For example, the memory may be configured to store one or more inflation pressures, pressure thresholds, blood pressures, heart rates, temperatures, $SpO_2$ values, patient identities, and/or other like information.

The system 10 can further include a user interface (not shown) configured to provide communication to the patient 14 or one or more operators. For example, the user interface could include a display configured to communicate and/or otherwise output one or more parameters or characteristics of the patient 14. The user interface may further include one or more speakers or other like audio devices configured to communicate and/or otherwise output information to the patient 14 and/or a user operator of the system 10. In some embodiments, the user interface may be connected to the communication device 46 and/or to the system controller 30. In such embodiments. In such embodiments, the user interface may be configured to receive, for example, audible control commands from the user. Accordingly, in such embodiments, the operation of one or more of the sensors 44, the system controller 30, and/or other components of the system 10 may be voice-activated and/or voice controlled during the various determination methods described herein. Further, the communication device 46 may facilitate connection to various tablets, laptops, cellular phones, and/or other known mobile devices. Such connectivity may enable the sensors 44, the system controller 30, and/or other components of the system 10 to be operated and/or otherwise controlled remotely via such devices, such as via applications running on such devices. Further, the use of such mobile devices may further facilitate voice-based operation and/or control of the system 10.

Figure 4:
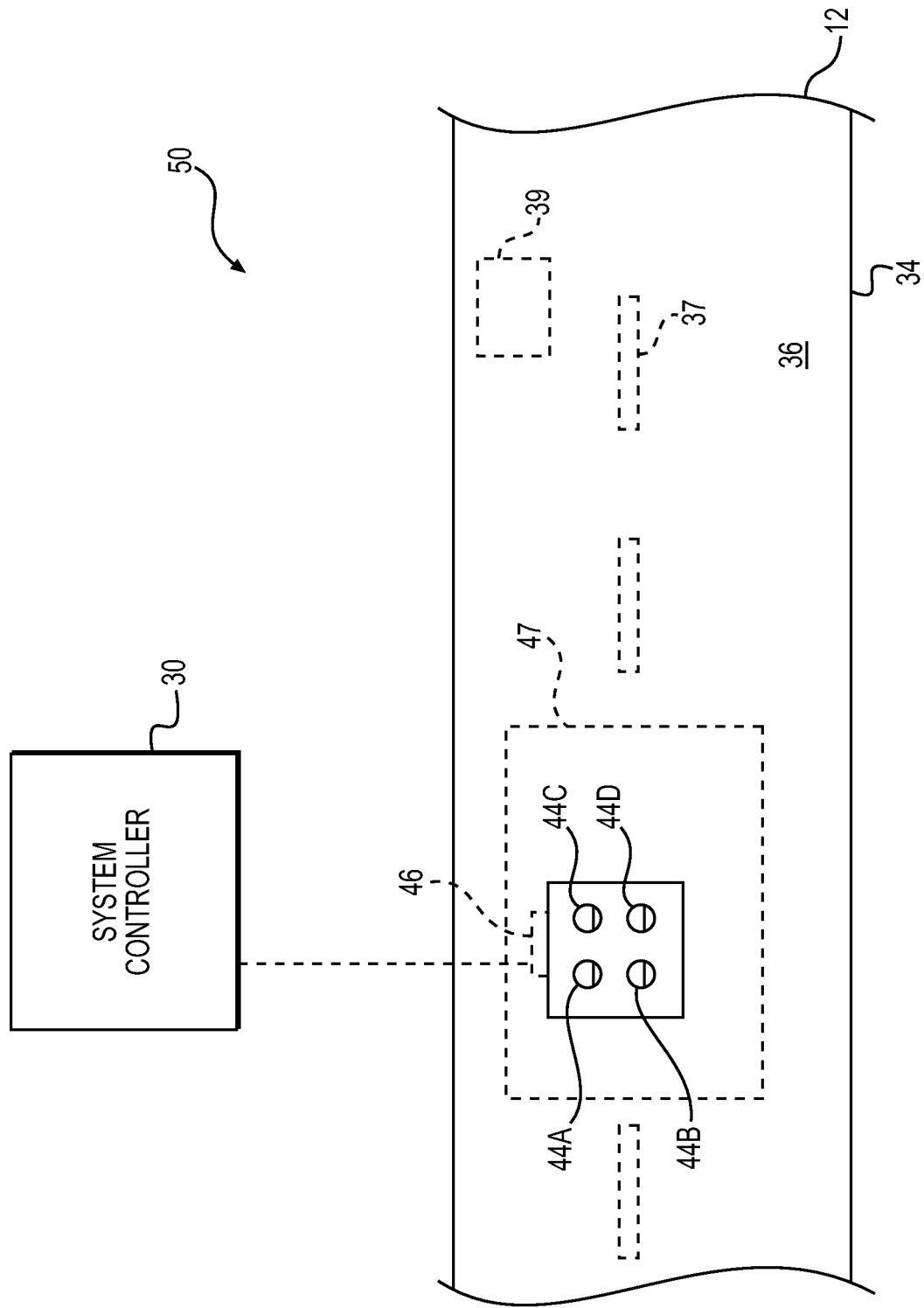
FIG. 4 illustrates a system according to another exemplary embodiment of the present disclosure.

FIG. 4 illustrates an additional system 50 according to an exemplary embodiment of the present disclosure. Wherever possible, like item numbers have been used throughout the present application to illustrate like components of the various systems described herein. For example, as shown in FIG. 4, the system 50 may include, among other things, an inflatable cuff 12, one or more sensors 44, and/or a system controller 30 operably and/or otherwise connected to the sensors 44. The cuff 12 of the system 50 may also include one or more alignment markers 37 as well as one or more information features 39. In the embodiment illustrated in FIG. 4, such alignment markers 37 and information features 39 may be disposed on the outer surface 34 of the cuff 12. Alternatively, in further exemplary embodiments, at least one of the alignment markers 37 and/or information features 39 may be disposed on the inner surface 36 of the cuff.

Additionally, in the system 50 illustrated in FIG. 4, at least one of the sensors 44 may be connected to the cuff 12. In such embodiments, the system 50 may also include one or more interrogation components 47 disposed at least partially within a field of view of at least one of the sensors 44. Such an exemplary interrogation component 47 is illustrated in dashed lines in FIG. 4. Alternatively, in further exemplary embodiments of the system 50, such interrogation components 47 may be omitted.

In the embodiment of the system 50 illustrated in FIG. 4, the sensors 44 may be disposed at any location on or within the cuff 12 in order to facilitate noninvasively determining a respective perimeter of the patient 14 when, for example, the cuff 12 is disposed around the limb 16 of the patient 14. For example, at least one of the sensors 44 may be disposed on, connected to, and/or formed integral with the inner surface 36. In such embodiments, at least one of the sensors 44 may be disposed substantially coplanar with the inner surface 36 of the cuff 12. In such embodiments, the inner surface 36 and/or the at least one sensor disposed coplanar therewith may be configured to contact the patient 14 at the measurement site during inflation and/or deflation of the cuff 12 about the limb 16. In such embodiments, at least one of the sensors 44 may be configured to contact, for example, the skin of the patient 14 during occlusion of the blood vessel 22, and may be configured to determine a temperature, blood pressure, blood oxygen saturation, and/or other respective parameter of the patient 14 during occlusion of the blood vessel 22.

In further exemplary embodiments, at least one of the sensors 44 may be disposed on, connected to, and/or formed integral with the outer surface 34. In such embodiments, the one or more sensors 44 disposed on the outer surface 34 may be configured to determine respective perimeters of the patient 14 via, for example, the inner surface 36 and/or via one or more interrogation components 47 disposed at least partially within a corresponding field of view of the sensor. It is understood that sensors 44 disposed on the outer surface 34 of the cuff 12 may have the advantage of being relatively easily accessible by the patient 14 and/or by a user of the system 50.

In still further embodiments, at least one of the sensors 44 may be disposed at least partially within the cuff 12 (i.e., at least partially between the outer surface 34 and the inner surface 36), or at least partially within a component of the cuff 12. For example, in such embodiments at least one of the sensors 44 may be disposed at least partially within, for example, the port 38 or the passage 40 defined by the port 38. In such embodiments, the at least one sensor may be configured to determine a respective parameter of the patient 14 via the port 38 and/or the passage 40. Further, in such embodiments, the at least one sensor may be configured to determine the respective parameter via the inner surface 36 and/or via one or more interrogation components 47 associated with the inner surface 36. Such interrogation components 47 may be substantially identical to those described above with respect to, for example, FIG. 3, and such interrogation components 47 may be disposed on and/or formed integrally with, for example, the inner surface 36. Additionally, one or more of the sensors 44 may be spaced from, positioned opposite, and/or otherwise disposed anywhere on the cuff 12 relative to one or more additional sensors 44. For example, each sensor may have a unique position on the cuff 12 relative to each of the other sensors 44.

Figure 5:
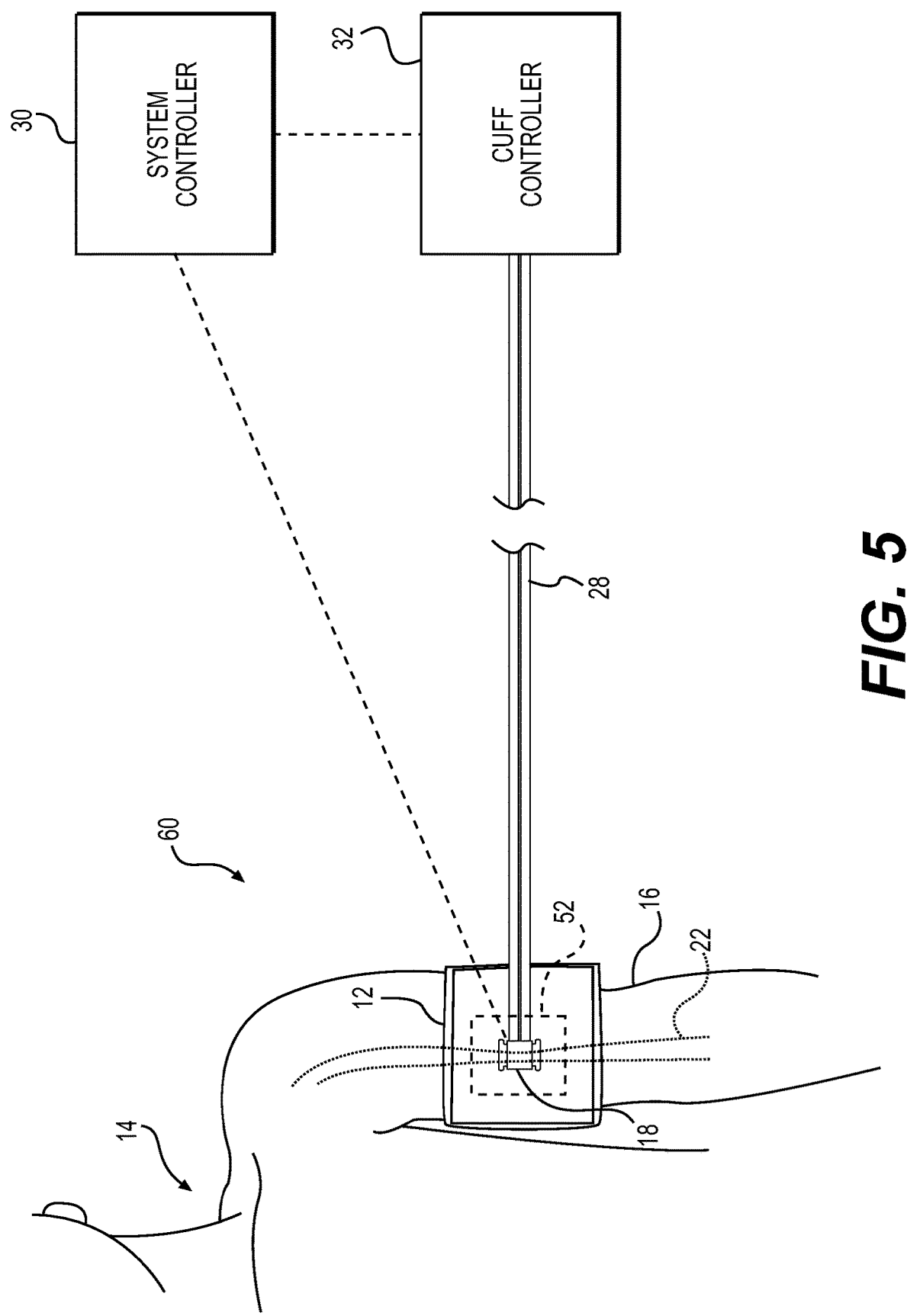
FIG. 5 illustrates a system according to still another exemplary embodiment of the present disclosure.
Figure 6:
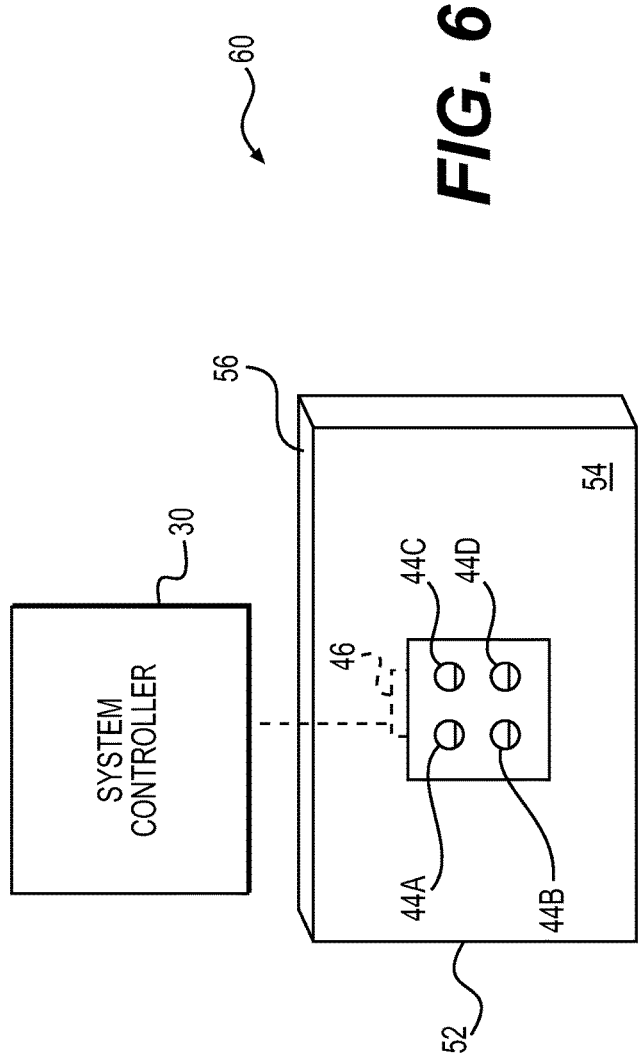
FIG. 6 illustrates an exemplary patch associated with the system shown in FIG. 5.
Figure 7:
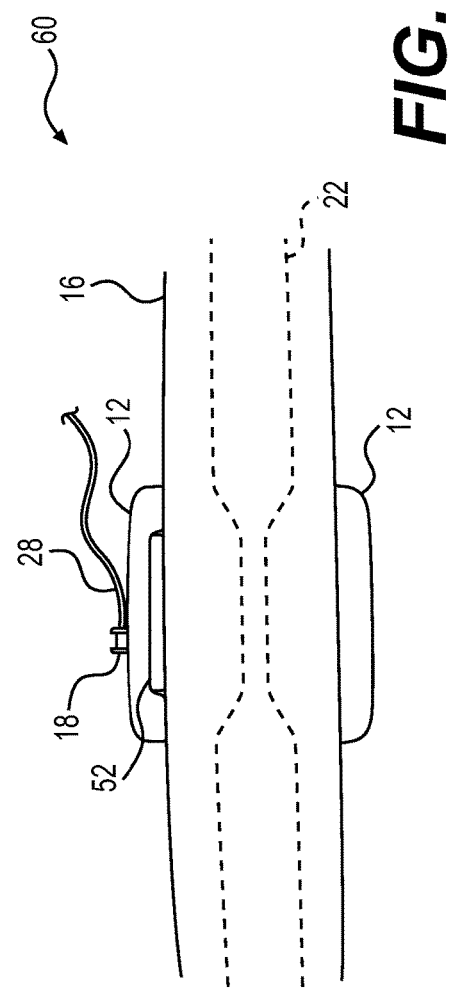
FIG. 7 illustrates an exemplary patch and an exemplary cuff associated with the system shown in FIG. 5.

FIGS. 5-7 illustrate an additional system 60 according to an exemplary embodiment of the present disclosure. As noted above, wherever possible, like item numbers have been used throughout the present application to illustrate like components of the various systems described herein. For example, as shown in FIGS. 5-7 the system 60 may include, among other things, an inflatable cuff 12, one or more sensors 44, and/or a system controller 30 operably and/or otherwise connected to the sensors 44. The system 60 may also include one or more patches 52 configured to be worn by the patient 14.

As shown in FIG. 6, the patch 52 may include a first surface 54 and a second surface 56 opposite first surface 54. The patch 52 may be substantially planar and may have any desirable thickness between the first surface 54 and the second surface 56. In exemplary embodiments, the patch 52 may be substantially square, substantially rectangular, substantially circular, and/or any other desirable shape. Additionally, the patch 52 may be configured to fit underneath the cuff 12 while the cuff 12 is disposed about the limb 16 of the patient 14. For example, in some embodiments it may be desirable for the patch 52 to be as thin as possible so as not to interfere with inflation or deflation of the cuff 12 and/or with occluding the blood vessel 22. In exemplary embodiments, the patch 52 may be between 1 mm and 5 mm thick, and in further embodiments, the patch 52 may be less than 1 mm thick. In further embodiments, however, the patch 52 may be disposed on and/or at a first measurement site of the patient 14, and the cuff 12 may be disposed at a second measurement site different than the first measurement site. For example, the patch 52 may be disposed on or at the forearm of an arm of the patient while the cuff 12 may be disposed around the bicep and tricep of the arm. In still further embodiments, the patch 52 may be disposed on, for example, a first arm of the patient 14 and the cuff 12 may be disposed on, for example, a second arm of the patient 14. In such embodiments, sensors 44 associated with the patch 52 may determine one or more parameters of the patient 14 at the first measurement site while the cuff 12 is inflated, deflated, and/or otherwise disposed at the second measurement site.

In exemplary embodiments, the first surface 54 may comprise a bottom surface of the patch 52 configured to contact and/or otherwise be removably connected to the patient 14. For example, the first surface 54 may be configured to be removably connected to a measurement site on, for example, the limb 16 of the patient 14. In such embodiments, the first surface 54 may include, for example, an adhesive configured to assist in removably attaching the first surface 54 to the limb 16.

One or more of the sensors 44 may be at least partially disposed on the first surface 54 or the second surface 56 of the patch 52. For example, as shown in FIG. 6, at least one of the sensors 44 may be disposed proximate, adjacent to, and/or substantially coplanar with the first surface 54. Alternatively, at least one of the sensors 44 may be disposed proximate, adjacent to, and/or substantially coplanar with the second surface 56. In still further embodiments, at least one of the sensors 44 may be disposed within the patch 52 such as, for example, substantially between the first surface 54 and the second surface 56. Although not shown in FIG. 6, in some embodiments the patch 52 may include one or more interrogation components 42. For example, such interrogation components 42 may be disposed on and/or formed substantially integral with the first surface 54 or the second surface 56. In such embodiments, the one or more interrogation components 42 may be disposed within the field of view of at least one of the sensors 44. For example, the interrogation components 42 may overlay at least one of the sensors 44. Alternatively, in further exemplary embodiments interrogation components 42 may be omitted.

As shown in FIG. 6, in exemplary embodiments the system 60 may also include a communication device 46 connected to one or more of the sensors 44. In such embodiments, the communication device 46 may be disposed on, for example, the first surface 54 or the second surface 56 of the patch 52. Alternatively, the communication device 46 may be disposed substantially between the first surface 54 and the second surface 56. As noted above, the communication device 46 may be configured to provide signals from at least one of the sensors 44 to the system controller 30. In such embodiments, the signals directed from the sensors 44 to the system controller 30 may be indicative of one or more of the parameters determined by the respective sensors 44. As described above, the system controller 30 may utilize information contained in such signals as inputs to one or more algorithms, neural networks, or other like components in determining a characteristic of the patient 14.

In addition to the components outlined above, the systems 10, 50, 60 described herein may include various other components as required, such as, for example, a power source and/or a user input device. One or more components described herein may be combined or may be separate independent components of the respective system. Moreover, the various components of the systems 10, 50, 60 could be integrated into a single unit or may operate as separate units. In operation, one or more processors can be configured to operate in conjunction with one or more software programs to provide the functionality of the systems 10, 50, 60. For example, one or more of the components described above with respect to the systems 10, 50, 60 may include one or more hardware components and/or one or more software components configured to control operation of such components and/or of the systems 10, 50, 60. It is understood that in the system 10 of FIGS. 1-3 in which the sensors 44 are disposed substantially within the cuff connector 18, the sensors 44 may determine various parameters of the patient 14 by viewing the measurement site (i.e., the skin of the limb 16 of the patient 14) via the interrogation component 42 of the cuff 12. In the system 50 of FIG. 4, on the other hand, the sensors 44 may determine various parameters of the patient 14 by viewing the measurement site via the inner surface 36 and/or the interrogation component 47. Moreover, in the system 60 of FIGS. 5-7, the sensors 44 coupled to the patch 52 may determine various parameters of the patient 14 by viewing the measurement site via substantially direct contact between the measurement site and the patch 52.

Figure 8:
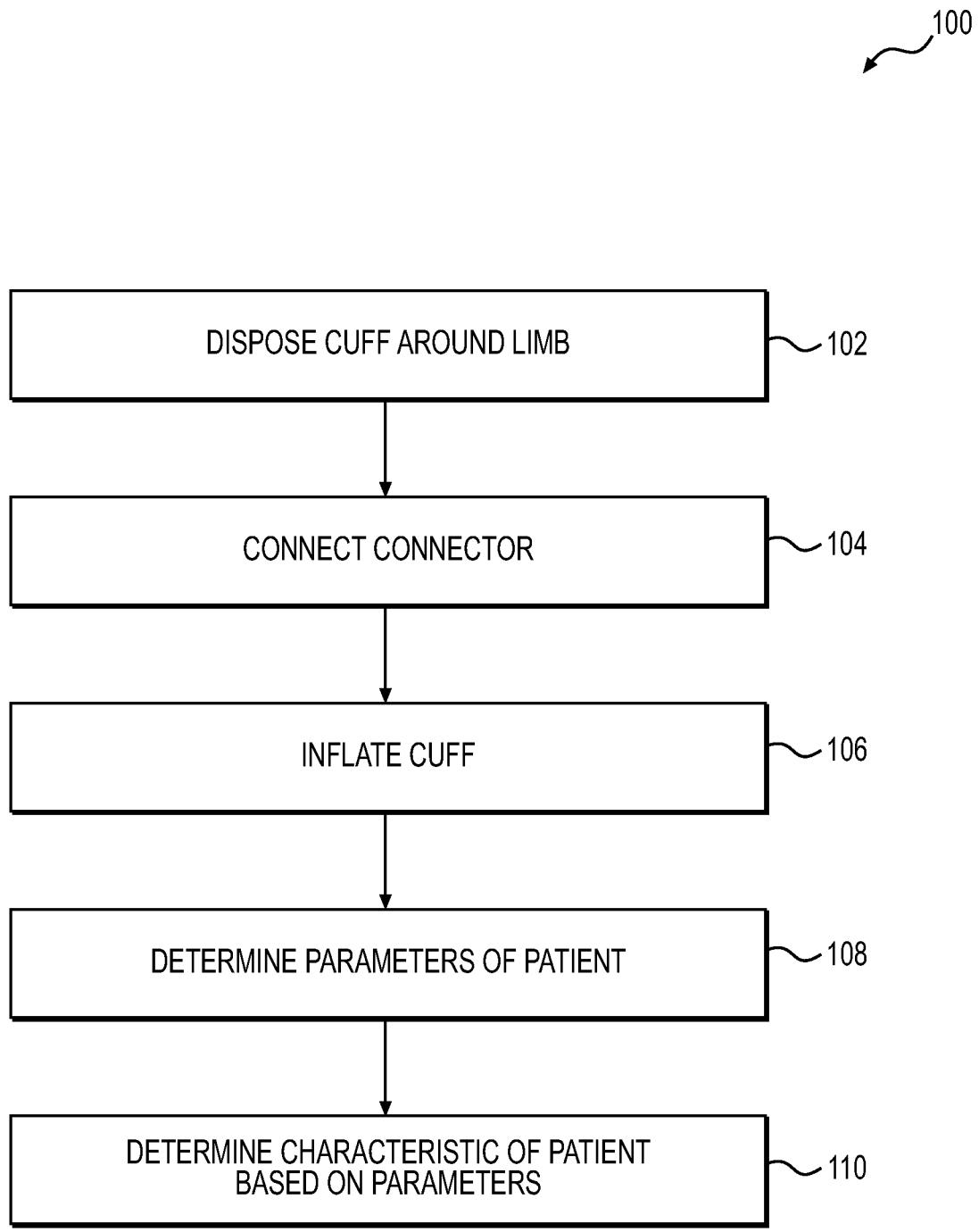
FIG. 8 illustrates a flow chart describing an exemplary method of the present disclosure.

As illustrated by the flow chart 100 shown in FIG. 8, in exemplary embodiments, methods of monitoring the patient 14 and/or determining a characteristic of the patient 14 may include determining one or more parameters associated with the patient 14 and, in particular, one or more parameters of the blood vessel 22 and/or of one or more measurement sites of the patient 14. Such methods may comprise oscillometric methods, auscultation methods, infrared temperature determination methods, pulse oximetry methods, Doppler measurement methods, and/or any other known patient monitoring methods. For example, such methods may include positioning and/or otherwise disposing the cuff 12 about a limb 16 of the patient 14 (Step: 102). In exemplary embodiments, a substantially deflated cuff 12 may be positioned around a portion of an arm of patient 14, such as above the elbow (i.e., circumferentially around the bicep and tricep). Additionally, at Step: 102 a healthcare professional and/or other user may substantially align one or more of the alignment markers 37 of the cuff 12 with the blood vessel 22 of the patient. Such alignment may include, for example, rotating the cuff 12 in a clockwise or counter-clockwise direction when the cuff 12 is disposed around the limb 16 until one or more of the alignment markers 37 extends substantially parallel to the blood vessel 22 and/or substantially overlays the blood vessel 22. Since it may not be possible for the healthcare professional to fully view the blood vessel 22, such alignment may be an approximation.

In exemplary embodiments of the system 50 in which one or more sensors 44 are connected to the cuff 12, substantially aligning one or more of the alignment markers 37 with the blood vessel 22 as described above may position the sensors 44 in close proximity to the blood vessel 22 at the measurement site. For example, aligning the cuff 12 in this way may position at least one of the sensors 44 such that it substantially overlays the blood vessel 22. In exemplary embodiments in which the cuff 12 includes one or more interrogation components 42, such alignment of the cuff 12 may also position at least one of the interrogation components 42 such that it also overlays the blood vessel 22 in order to facilitate parameter determinations by the sensors 44.

In some embodiments, information particular to the patient 14 may be read from a patient identifier associated with the information feature 39 disposed on the outer surface 34 of the cuff 12. Such information may be read, for example, by one or more of the sensors 44 connected to the cuff connector 18. Alternatively, such information may be read by a separate scanner, RFID reader, barcode reader, or other like device. Additionally, such information may be read prior to disposing the cuff 12 on the limb 16 of the patient 14, or after the cuff 12 has been disposed on the limb 16. As noted above, and still further exemplary embodiments, such information may be read from an information feature 48 disposed within the field of view of one or more of the sensors 44 after the cuff connector 18 has been removably connected to the cuff 12. In such embodiments, the cuff 12 may be configured for use with a particular patient 14. In such embodiments, the patient identifier and/or other information included in the information feature 39 may identify the patient 14 with which the cuff 12 is associated. In this way, the information feature 39 may facilitate leaving the cuff 12 disposed on or around a limb 16 of the patient 14 for patient monitoring procedures lasting for extended periods of time, and/or for procedures taking place at multiple locations throughout the healthcare facility. Further, information provided by the information feature 39 may, in some embodiments, be used by the system controller 30 in determining one or more characteristics of the patient 14 described herein.

At Step: 104, the user may fluidly connect the cuff connector 18 to the cuff 12. For example, at Step: 104, the user may removably connect the extension 24 to the port 38 associated with the cuff 12 such that a fluid connection is formed between the port 38 and the extension 24. In exemplary embodiments, Step: 104 may further include connecting one or more of the retention components 22 to the port 38 and/or other portions of the cuff 12 to facilitate a substantially fluid tight connection between the cuff 12 and the cuff connector 18. Additionally, in some embodiments removably connecting the cuff connector 18 to the cuff 12 at the port 38 may position at least one of the sensors 44 connected to the cuff connector 18 such that at least a portion of the blood vessel 22 is disposed at least partially within the field of view of the sensor. It is understood that aligning the cuff 12 with the blood vessel 22 as described above with regard to Step: 102 may position an interrogation component 42 between, for example, the port 38 and the blood vessel 22. In such embodiments, removably connecting the cuff connector 18 to the cuff 12 may position the sensors 44 such that the interrogation component 42 is disposed at least partially within the field of view of at least one of the sensors 44.

At Step: 106, the system controller 30 may control the cuff controller 32 to inflate the cuff 12 automatically (such as in accordance with a predetermined inflation protocol) or manually (such as in the case of a manually operated inflation bulb). It is understood that inflating the cuff 12 at Step: 106 may at least partially occlude the blood vessel 22. In further embodiments, the blood vessel 22 may be substantially completely occluded at Step: 106 such that substantially no (i.e., negligible) blood may flow through the blood vessel 22.

At Step: 108, the sensors 44 and/or the system controller 30 may determine one or more parameters associated with the blood vessel 22, and/or with the measurement site generally, while the cuff 12 is at least partially inflated and/or while the cuff connector 18 is connected to the cuff 12. For example, parameters determined while the blood vessel 22 is at least partially occluded may include a systolic blood pressure, and such a blood pressure may be determined based on variations in the pressure within the cuff 12. For example, the cuff controller 32 may inflate the cuff 12 to an occlusion pressure that is greater than or equal to a systolic pressure of blood vessel 22, and the sensors 44 may measure and/or otherwise determine oscillations in cuff pressure according to one or more known oscillometric methods. In exemplary embodiments, the cuff controller 32 may utilize such information as inputs to one or more oscillometric pressure algorithms and may determine, for example, a systolic pressure associated with the blood vessel 22 based on such information. Alternatively, once the cuff 12 is inflated to the occlusion pressure, the user may utilize known auscultation methods known in the art to determine a systolic pressure associated with the blood vessel 22. It is understood that such methods may also be used at Step: 108 to determine a diastolic pressure associated with the blood vessel 22. Additionally, at Step: 108 the sensors 44 may determine one or more additional parameters of the patient 14. Such additional parameters may include, but are not limited to, for example, a temperature of the measurement site, a heart rate, a blood oxygen saturation, a venous blood pressure, and/or any other like parameter indicative of, for example, the health or status of the patient 14. It is understood that in embodiments of the system 50 in which the sensors 44 are connected to the cuff 12, any of the parameters described herein may be determined at Step: 108 with or without the cuff connector 18 being connected to the cuff 12. Moreover, at Step: 108, one or more of the sensors 44 may generate signals indicative of the respective parameter determined thereby, and the sensors 44 may direct such signals to the system controller 30 via the communication device 46.

At Step: 110, the system controller 30 may determine one or more characteristics of the patient 14 based on at least one of the parameters determined by the respective sensors 44. As noted above, the characteristics of the patient 14 determined by the system controller 30 at Step: 110 may comprise any of the parameters described herein with respect to the sensors 44. Further, in exemplary embodiments a characteristic determined by the system controller 30 at Step: 110 may comprise a first parameter as modified by one or more additional parameters determined by the respective sensors 44. At step: 110, the system controller 30 may utilize information contained in the one or more signals received from the sensors 44 as inputs into one or more blood pressure algorithms, temperature algorithms, SpO$_2$ algorithms, heart rate algorithms, and/or other like algorithms or neural networks. Such components may combine, modify, and/or otherwise utilize such inputs in determining the resulting characteristic of the patient 14.

In one example, at Step: 110 the characteristic of the patient 14 determined by the system controller 30 may be blood pressure. In such an example, at least one of the sensors 44 (e.g., a first sensor 44a) may comprise one or more transducers or other like blood pressure determination components. The sensor 44a may generate one or more signals indicative of a determined blood pressure of the patient 14 during inflation and/or deflation of the cuff 12, and may direct such signals to the system controller 30 via the communication device 46. In such an example, an additional one of the sensors 44 (e.g. a second sensor 44b) may comprise one or more thermopiles or other like temperature determination components. The sensor 44b may generate one or more signals indicative of a determined temperature of the patient 14 at, for example, the measurement site at which the cuff 12 is located. The sensor 44b may direct such signals to the system controller 30 via the communication device 46. In such an example, the signals sent by the respective sensors 44 may include timestamps, encryption information, and/or other like information enabling the system controller 30 to identify corresponding signals determined by the sensors 44.

Upon receiving the corresponding signals, the system controller 30 may, at Step: 110, enter information carried by the corresponding signals into the one or more algorithms or neural networks described above. In the above example in which the characteristic of the patient 14 determined by the system controller 30 is blood pressure, the system controller 30 may, for example, utilize a blood pressure determination algorithm in which the blood pressure determined by the first sensor 44a is given significant weight, and in which the temperature determined by the second sensor 44b is given relatively less weight, but is taken into account during the ultimate blood pressure determination in order to improve the accuracy of the blood pressure determined at Step: 110. Although not explicitly described in the present example, it is understood that one or more of the SpO$_2$, heart rate, and/or other parameters of the patient determined by the remaining sensors 44 may also be taken into account during the ultimate blood pressure determination in order to improve the accuracy of the blood pressure determined at Step: 110. Upon determining such characteristics at Step: 110, the system controller 30 may output the determined characteristics using one or more user interfaces (not shown) or other like devices known in the art.

In another example, the characteristic of the patient 14 determined by the system controller 30 at Step: 110 may be SpO$_2$ and/or an average SpO$_2$ of the patient 14. In such an example, at least one of the sensors 44 (e.g., the first sensor 44a) may comprise one or more pulse oximeters and/or other like SpO$_2$ determination devices. The sensor 44a may determine a plurality of instantaneous SpO$_2$ values of the patient 14 at Step: 108 during inflation and/or deflation of the cuff 12. The sensor 44a may also direct one or more signals indicative of the instantaneous SpO$_2$ values to the system controller 30 via the communication device 46. In such an example, an additional one of the sensors 44 (e.g. the second sensor 44b) may comprise one or more transducers or other like blood pressure determination components. The sensor 44b may determine the blood pressure of the patient 14 at Step: 108 during inflation and/or deflation of the cuff 12, and substantially simultaneously with the $SpO_2$ determinations of the first sensor 44a. The sensor 44b may also generate one or more signals indicative of determined blood pressure values of the patient 14 as the cuff 12 is inflated and while the first sensor 44a is determining $SpO_2$. The sensor 44b may direct such signals to the system controller 30 via the communication device 46.

It is understood that blood passing through the arteries of the patient 14 (i.e., arterial blood flow) may contain various amounts of oxygen, while blood passing through the veins of the patient 14 (i.e., venous blood flow) may be substantially without oxygen. Accordingly, in some embodiments the system 10 may utilize $SpO_2$ measurements associated with at least the arterial blood flow of the patient 14 to determine the average $SpO_2$ of the patient 14 at Step: 110. In such embodiments, at least a portion of the instantaneous $SpO_2$ measurements associated with the venous blood flow of the patient 14 may be excluded when determining the average $SpO_2$ of the patient 14 at Step: 110. For example, in the process described above in which the second sensor 44b determines the blood pressure of the patient 14 as the first sensor 44a determines instantaneous $SpO_2$ values at Step: 108, the system controller 30 may utilize only the $SpO_2$ values determined at cuff pressures approximately greater than (i.e., above) the occlusion pressure of the vein or other blood vessel 22 around which the cuff 12 is disposed (i.e., proximate the measurement site) when determining the average $SpO_2$ of the patient 14 at Step: 110. In such example embodiments, in order to avoid patient discomfort the system 10 may also only utilize the instantaneous $SpO_2$ values determined at cuff pressures approximately less than (i.e., below) the diastolic and/or occlusion pressure of the artery or other blood vessel 22 around which the cuff 12 is disposed. Although such occlusion pressures may vary depending on, for example, the age, health, weight, gender, and/or ethnicity of the patient 14, example venous occlusion pressures may typically be between approximately 15 mmHg and approximately 25 mmHg, while example arterial occlusion pressures may typically be between approximately 60 mmHg and approximately 100 mmHg. In such example embodiments, at Step: 110 the average $SpO_2$ of the patient 14 may be determined based on and/or informed by the corresponding blood pressure values described above.

In yet another example, the characteristic of the patient 14 determined by the system controller 30 at Step: 110 may be core temperature. In such an example, at least one of the sensors 44 (e.g., the first sensor 44a) may comprise one or more thermopiles and/or other like temperature determination devices. The sensor 44a may determine the surface temperature of the limb 16 of the patient 14, or of any other like measurement site, at Step: 108 during inflation and/or deflation of the cuff 12. The sensor 44a may also direct one or more signals indicative of determined temperature values to the system controller 30 via the communication device 46. In such an example, an additional one of the sensors 44 (e.g. the second sensor 44b) may comprise one or more transducers or other like blood pressure determination components. The sensor 44b may determine the blood pressure of the patient 14 at Step: 108 during inflation and/or deflation of the cuff 12, and substantially simultaneously with the surface temperature determinations of the first sensor 44a. The sensor 44b may also generate one or more signals indicative of determined blood pressure values of the patient 14 as the cuff 12 is inflated and while the first sensor 44a is determining the temperature of the measurement site. The sensor 44b may direct such signals to the system controller 30 via the communication device 46. In such embodiments it is understood that the temperature, pressure, flow rate, and/or other characteristics of blood passing through the blood vessel 22 around which the cuff 12 is disposed may have an effect on, for example, the surface temperatures determined by the first sensor 44a at Step: 108. For example, due to the presence of blood in the blood vessel 22 the temperatures determined by the first sensor 44a while the blood vessel 22 is substantially unoccluded (i.e., unoccluded measurement site temperatures) may be relatively greater than the temperatures determined by the first sensor 44a while the blood vessel 22 is substantially occluded (i.e., occluded measurement site temperatures). Additionally, in some embodiments the extent to which such occluded measurement site temperatures differ from such unoccluded measurement site temperatures may depend upon, for example, the age, health, weight, gender, and/or ethnicity of the patient 14, among other things. For example, such temperature differences may be larger in patients 14 of average weight and/or body mass index than in bariatric patients 14 since the blood vessel 22 may be located relatively closer to the cuff 12 and/or the first sensor 44a in such average weight patients 44. In any of the example embodiments described above, the core temperature of the patient 14 determined at Step: 110 may be determined based on and/or informed by one or more correlations related to, one or more differences between, one or more rates of change, one or more shapes of a change profile, and/or other relationships associated with the unoccluded measurement site temperatures and the occluded measurement site temperatures. For example, one or more algorithms, neural networks, look-up tables, or other like components may be selected, modified, and/or otherwise utilized by the system controller 30 to determine the core temperature of the patient 14 at Step: 110 based on one or more such relationships.

At Step: 110, the cuff controller 32 may also deflate the cuff 12 automatically and/or manually similar to the inflation protocol described above. Additionally, at Step: 110 the user may determine one or more additional parameters and/or corresponding characteristics of the patient 14 associated with blood vessel 22 while the cuff 12 is being deflated and/or while the cuff 12 is substantially deflated. Further, it is understood that the methods described above with respect to the flow chart 100 shown in FIG. 8 may be employed by any of the systems 10, 50, 60 described herein.

Figure 9:
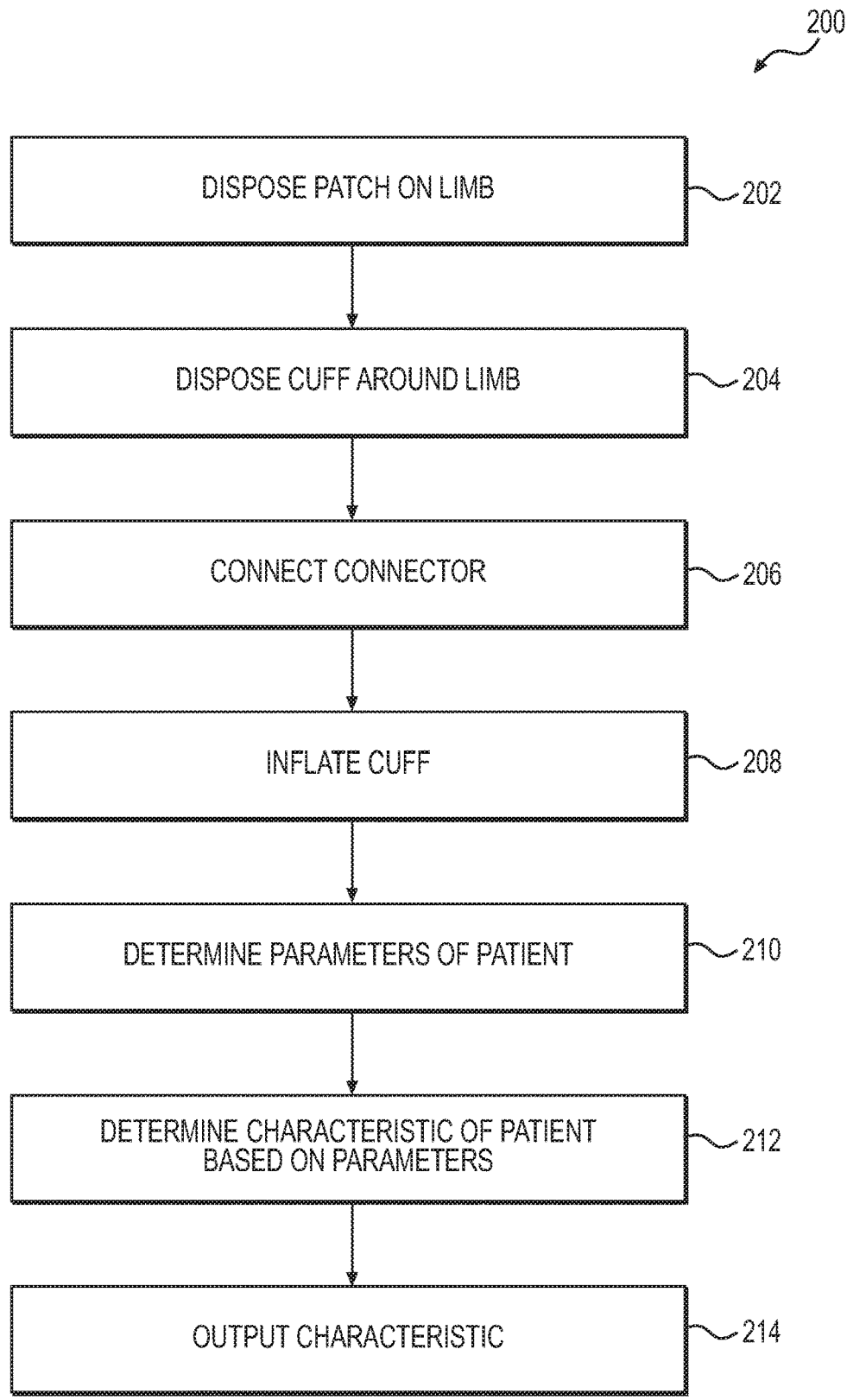
FIG. 9 illustrates a flow chart describing another exemplary method of the present disclosure.

In further exemplary embodiments, however, methods of determining various characteristics of the patient 14 utilizing the system 60 may incorporate greater than, less than, and/or different steps than those described with respect to the flow chart 100 shown in FIG. 8. For example, FIG. 9 shows a flow chart 200 illustrating a method of determining a characteristic of the patient 14 according to an additional exemplary embodiment of the present disclosure, and one or more of the steps included in the method illustrated by the flow chart 200 may be tailored to the system 60. For example, at Step: 202, the user may adhere, connect, and/or otherwise dispose a patch 52 on the limb 16 of the patient 14. In such embodiments, at least one of the first surface 54 and the second surface 56 may include an adhesive or other like material configured to assist in substantially securely removably connecting the patch 52 to the limb 16 at the desired measurement site. For example, in exemplary embodiments in which one or more of the sensors 44 is connected to the patch 52 adjacent, proximate, and/or substantially coplanar with the first surface 54, the first surface 54 may be provided with such a material to assist in connecting the first surface 54 to the limb 16 at the measurement site. Additionally, at Step: 202 the user may position the patch 52 such that at least one of the sensors 44 is substantially aligned with the blood vessel 22 and/or such that the blood vessel 22 is at least partially disposed within a field of view of at least one of the sensors 44. Positioning the patch 52 in this way may assist one or more of the sensors 44 in determining a respective parameter of the patient 14. Although not illustrated in FIGS. 5-7, in exemplary embodiments, the patch 52 may include one or more alignment markers 37 to assist in positioning the patch 52.

At Step: 204, the user may dispose the cuff 12 around the limb 16 of the patient 14. Additionally, at Step: 204, the user may dispose the cuff 12 around at least a portion of the patch 52. As illustrated in at least FIG. 7, in one example the cuff 12 may be disposed around a limb 16 and the patch 52 such that the patch 52 is substantially completely covered by the cuff 12 and is disposed between the limb 16 and the cuff 12. As noted above, in some embodiments the thickness of the patch 52 may be minimized so as to reduce interference with the cuff 12 on the cuff 12 is disposed around limb 16. Minimizing the thickness of the patch 52 may also improve the efficiency of the cuff 12 in substantially occluding the blood vessel 22 and the sensitivity and/or accuracy of the sensors 44 in determining respective parameters of the patient 14.

At Step: 206, the user may removably connect the cuff connector 18 to the port 38 of the cuff 12, thereby forming a substantially fluid tight seal between the port 38 and, for example, the extension 24 of the cuff connector 18. At Step 208, the system controller 30 may control the cuff controller 32 to at least partially inflate the cuff 12. Such inflation at Step: 208 may be substantially similar to the inflation described above with respect to Step: 106 of FIG. 8. At Step: 210, at least one of the sensors 44 connected to the patch 52 may determine a respective parameter of the patient 14 while the cuff 12 is at least partially inflated and/or while the blood vessel 22 is at least partially occluded. Such partial occlusion of the blood vessel 22 is illustrated in FIG. 7.

It is understood that in additional exemplary embodiments in which the patch 52 is removably connected to the limb 16, at least one of the sensors 44 described herein may comprise, for example, an infrared and/or a capacitance sensor connected to the cuff 12. For example, a capacitance sensor 44a may be connected to the cuff 12 as described above with regard to one or more of the sensors 44 disclosed in FIG. 4. Such a capacitance sensor 44a may be configured to determine a respective perimeter of the patient 14 based on a capacitance of at least a portion of the cuff 12 and/or at least a portion of the patch 52.

For example, such a capacitance sensor 44a may interrogate at least a portion of the patch 52 by propagating one or more capacitive signals through the limb 16 and/or the artery 22. Such signals may be, for example, absorbed and/or reflected by the patch 52, and the capacitance sensor 44a may be configured to receive at least a portion of the signal reflected by the patch 52. In such embodiments, the capacitance sensor 44a may be configured to determine, for example, a temperature of the measurement site, electrocardiographic information indicative of, among other things, the electrical activity of the heart of the patient 14, and/or other like parameters at Step: 210.

In such embodiments, the capacitance sensor 44a connected to the cuff 12 may be positioned at any location relative to the patch 52 in order to conveniently transmit and/or receive capacitive signals. For example, in an embodiment in which the patch 52 is disposed substantially overlaying the bicep of the patient 14, the cuff 12 may be positioned about the limb 16 such that at least the capacitance sensor 44a is disposed opposite the patch 52, such as overlaying the tricep of the patient 14. In such embodiments, the capacitance sensor 44a may be disposed capacitively close to the patch 52 to facilitate the transmission and/or receipt of such capacitive signals. Additionally, it is understood that such capacitive signals may comprise, for example, counts or other like capacitive signals known in the art. In such embodiments, the value of such counts or other like capacitive signals may be provided to the system controller 30 via one or more signals sent by the capacitance sensor 44a by the communication device 46. It is also understood that such a capacitance sensor 44a and exemplary patch 52 may also be utilized and/or otherwise included in any of the systems 10, 50, 60 described herein.

At Step: 212, the system controller 30 may determine one or more characteristics of the patient 14 based on one or more of the parameters determined by the respective sensors 44 at Step: 210. Similar to the determinations noted above with respect to Step: 110 of FIG. 8, the characteristics of the patient 14 determined by the system controller 30 at Step: 212 may comprise any of the parameters described herein with respect to the sensors 44. Further, in exemplary embodiments a characteristic determined by the system controller 30 at Step: 212 may comprise a first parameter as modified by one or more additional parameters determined by the respective sensors 44. At step: 212, the system controller 30 may utilize information contained in the one or more signals received from the sensors 44 as inputs into one or more blood pressure algorithms, temperature algorithms, $SpO_2$ algorithms, heart rate algorithms, and/or other like algorithms or neural networks. Such components may combine, modify, and/or otherwise utilize such inputs in determining the resulting characteristic of the patient 14. Upon determining such characteristics at Step: 214, the system controller 30 may output the determined characteristics using one or more user interfaces (not shown) or other like devices known in the art. At Step: 212, the cuff controller 32 may also deflate the cuff 12 automatically and/or manually similar to the inflation protocol described above. Additionally, at Step: 212 the system controller 30 may determine one or more additional parameters and/or corresponding characteristics of the patient 14 associated with blood vessel 22 while the cuff 12 is being deflated and/or while the cuff 12 is substantially deflated.

Exemplary embodiments of the present disclosure may provide systems and methods for determining various vital signs and/or other characteristics of patients 14 using a single bundle of sensors 44. For example, a plurality of such sensors 44 may be associated with a standard blood pressure cuff 12 and/or a cuff connector 18 utilized to inflate and/or deflate such a cuff 12. In further exemplary embodiments, such a plurality of sensors 44 may be associated with one or more surface patches 52 capable of being removably connected to a limb 16 of the patient 14. In still further embodiments, one or more of the sensors 44 described herein may be connected to one or more of a patch 52, a cuff 12, and/or a cuff connector 18 to facilitate determining various respective parameters of the patient 14. By minimizing the number of separate and/or different devices utilized to determine various parameters of the patient 14, each of the embodiments described herein may reduce the amount of time as well as the complexity associated with evaluating and/or treating the patient 14 at a healthcare facility.

Moreover, in embodiments of the present disclosure a parameter determined by one or more sensors 44 may be validated and/or otherwise modified using one or more additional, but different, parameters determined by one or more additional sensors 44. As a result, the accuracy and/or reliability of the characteristic determinations made by the system controller 30 may be improved. Accordingly, the systems and methods described herein may provide improvements over known healthcare systems and methods.

Other embodiments of the present disclosure will be apparent to those skilled in the art from consideration of the specification and practice of the disclosure contained herein. It is intended that the specification and examples be considered as exemplary only, with a true scope and spirit of the present disclosure being indicated by the following claims.

What is claimed is:

1. A system configured to determine a characteristic of a patient, comprising:
    a connector configured to removably connect with a port of an inflatable blood pressure cuff, the connector comprising a fluid passage configured to
        receive pressurized fluid, and
        direct the pressurized fluid to exit the connector via an opening of the connector formed at an end of the fluid passage; and
    a plurality of sensors connected to the connector, wherein:
        each sensor of the plurality of sensors is characterized by a respective field of view and is configured to noninvasively determine a respective parameter of the patient,
        the respective parameter determined by each sensor is different from parameters determined by remaining sensors of the plurality of sensors, and
        the plurality of sensors is positioned opposite the opening such that the fluid passage is disposed at least partly within the respective field of view of each sensor of the plurality of sensors.

2. The system of claim 1, further including a communication device connected to the connector and operably connected to the plurality of sensors, the communication device being configured to wirelessly transmit signals from the plurality of sensors to a controller.

3. The system of claim 1, further including a controller in communication with the plurality of sensors, the controller configured to determine the characteristic of the patient based on at least a first parameter determined by a first sensor of the plurality of sensors and a second parameter determined by a second sensor of the plurality of sensors.

4. The system of claim 1, wherein the connector further includes:
    a retention component configured to apply a retention force to the port when the connector is removably connected to the port;
    a seal configured to form a substantially fluid-tight connection with the port when the connector is removably connected to the port; and
    a substantially hollow extension protruding from a top surface of the connector and defining the opening.

5. The system of claim 1, wherein a sensor of the plurality of sensors comprises a reading device, a camera, or a sound sensor.

6. The system of claim 1, further including the inflatable blood pressure cuff, and an interrogation component disposed at a fixed location on the blood pressure cuff, the interrogation component being positioned at least partially within a field of view of at least one sensor of the plurality of sensors when the connector is connected to the port, the interrogation component being configured to facilitate determination of at least one parameter of the patient by the at least one sensor.

7. The system of claim 6, wherein the interrogation component comprises an infrared-transparent window disposed on an inner surface of the cuff, and the at least one sensor comprises an infrared sensor.

8. The system of claim 6, wherein the interrogation component includes an information feature providing an occlusion efficiency particular to the cuff.

9. The system of claim 6, wherein the cuff comprises a patient identifier disposed at least partially within the field of view of the at least one sensor when the connector is connected to the port, the patient identifier providing information particular to the patient.

10. The system of claim 6, wherein the cuff comprises an alignment marker disposed on an outer surface of the cuff, the alignment marker being configured such that when the cuff is disposed around a limb of the patient with the alignment marker substantially overlaying a blood vessel of the patient, the blood vessel will be disposed at least partially within a field of view of at least one sensor of the plurality of sensors when the connector is releasably connected to the port.

11. The system of claim 1, wherein the plurality of sensors comprises at least one of a blood pressure sensor, a temperature sensor, a blood oxygen saturation sensor, a heart rate sensor, and a Doppler sensor, and wherein the system further includes a cuff controller configured to supply the pressurized fluid to the connector.

12. A method of manufacturing a system, the method comprising:
    providing a connector configured to removably connect with a port of an inflatable blood pressure cuff, the connector comprising a fluid passage configured to
        receive pressurized fluid and
        direct the pressurized fluid to exit the connector via an opening of the connector formed at an end of the fluid passage; and
    connecting a plurality of sensors to a portion of the connector, the portion of the connector being located proximate the fluid passage, wherein:
        each sensor of the plurality of sensors is characterized by a respective field of view and is configured to noninvasively determine a respective parameter of a patient,
        the respective parameter determined by each sensor is different from parameters determined by remaining sensors of the plurality of sensors, and
        the plurality of sensors is positioned opposite the opening such that the fluid passage is disposed at least partly within the respective field of view of each sensor of the plurality of sensors.

13. The method of claim 12, further including connecting a communication device to the connector and operably connecting the communication device to the plurality of sensors, the communication device being configured to wirelessly transmit signals from the plurality of sensors to a controller.

14. The method of claim 12, further including providing a controller in communication with the plurality of sensors, the controller configured to determine a characteristic of the patient based on at least a first parameter determined by a first sensor of the plurality of sensors and a second parameter determined by a second sensor of the plurality of sensors.

15. The method of claim 12, wherein the connector further includes:
    a substantially hollow extension protruding from an outer surface of the connector and defining at least part of the fluid passage; and a retention component configured to apply a retention force to the port when the connector is removably connected to the port, at least part of the retention component extending opposite an outer surface of the extension.

16. The method of claim 12, further including coupling a seal to the connector, the seal being configured to form a substantially fluid-tight connection with the port when the connector is removably connected to the port.

17. A system configured to determine a characteristic of a patient, comprising:
a connector configured to removably connect with a port of an inflatable blood pressure cuff, the connector comprising a fluid passage configured to
receive pressurized fluid and
direct the pressurized fluid to exit the connector via an opening of the connector;
a plurality of sensors disposed at fixed locations on the connector, wherein:
each sensor of the plurality of sensors is characterized by a respective field of view and is configured to noninvasively determine a respective parameter of the patient,
the respective parameter determined by each sensor is different from parameters determined by remaining sensors of the plurality of sensors, and
the plurality of sensors is positioned opposite the opening such that the fluid passage is disposed at least partly within the respective field of view of each sensor of the plurality of sensors;
a first controller fluidly connected to the connector and configured to supply the pressurized fluid to the connector; and
a second controller operably connected to the first controller and to the plurality of sensors, the second controller being configured to determine the characteristic of the patient based at least in part on a first signal received from a first sensor of the plurality of sensors and a second signal received from a second sensor of the plurality of sensors.

18. The system of claim 17, further including a communication device connected to the connector and operably connected to the plurality of sensors, the communication device being configured to wirelessly transmit the first signal and the second signal to the controller.

19. The system of claim 18, further comprising at least one of a reading device and a camera connected to the connector and operably connected to the communication device, the communication device being configured to wirelessly transmit a third signal from the at least one of the reading device and the camera to the controller.

20. The system of claim 19, wherein the third signal includes information indicative of at least one of a patient identifier uniquely identifying the patient, and an occlusion efficiency particular to the blood pressure cuff,
the system further comprising the blood pressure cuff, wherein the information is provided by an information feature connected to the cuff.

21. The system of claim 1, wherein the connector further includes a substantially hollow extension protruding from a top surface of the connector and defining at least part of the fluid passage, at least one sensor of the plurality of sensors being configured to determine a respective parameter of the patient via the extension.

22. The system of claim 1, wherein removably connecting the connector with the port
places the connector in direct contact with the port, and
positions at least one sensor of the plurality of sensor such that an internal portion of the cuff is disposed within the field of view of the at least one sensor.

* * * * *